US006884779B2

(12) United States Patent
Verschueren et al.

(10) Patent No.: US 6,884,779 B2
(45) Date of Patent: Apr. 26, 2005

(54) SMAD-INTERACTING POLYPEPTIDES AND THEIR USE

(75) Inventors: Kristin Verschueren, Everberg (BE); Jacques Remacle, Hannut (BE); Danny Huylebroeck, Liedekerke (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 309 days.

(21) Appl. No.: 09/964,238

(22) Filed: Sep. 26, 2001

(65) Prior Publication Data

US 2002/0035246 A1 Mar. 21, 2002

Related U.S. Application Data

(62) Division of application No. 09/449,285, filed on Nov. 24, 1999, now Pat. No. 6,313,280, which is a continuation of application No. PCT/EP98/03193, filed on May 28, 1998.

(30) Foreign Application Priority Data

Jun. 2, 1997 (EP) .............................................. 97201645

(51) Int. Cl.[7] .............................................. C07K 14/00
(52) U.S. Cl. ........................ 514/12; 530/300; 530/350
(58) Field of Search ................................ 530/300, 350; 514/2

(56) References Cited

PUBLICATIONS

Chen et al. Oct. 24, 1996. Nature 383:691–696.*
Laguna et al. Oct. 31, 1996; Nature 383:832–836.*
Zhang et al. Sep. 12, 1996; Nature 383:168–172.*
Databse Embl Est 16: "Mus musculus cDNA clone 584313 5' DNA–binding protein", Accession No. AA125512, Nov. 26, 1996, XP002084026, Compare nucleotides 1–461 of AA125512 with nucleotides 1567–2027 in Seq. ID No.: 1, 1 page.
Databse Embl Hum1: "Human mRNA for KIAA0150 gene, partial cds.", Accession No. D63484, Aug. 3, 1996, XP002084022, compare nucleotides 1–2908 of D63484 with nucleotides 38–2952 in Seq. ID No.: 3, 5 pages.
Databse Embl Emrod: "Mouse Wnt–7b mRNA, completet cds.", Accession No. M89802, Apr. 3, 1992, XP002084023, cited in the application compare nucleotides 74–529 in M89802 with nucleotides 391–848 in Seq. ID No.:8, 2 pages.
Databse Embl Est 16: "Stratagene mouse melanoma. Mus musculus cDNA clone 651678 5", Accession No. AA212269, Feb. 3, 1997, XP002084024, cited in the application Compare nucleotides 1–432 of AA212269 with nucleotides 930–1362 in Seq. ID No.:10, 1 page.

Databse Embl EMHUM1: "Homo sapiens mRNA for KIAA0569 protein, complete cds.", Accession No. AB011141, Apr. 10, 1998, XP002084025, compare nucleotides 1250–4249 in AB011141 with nucleotides 8–3007 in Seq. ID No.:1, 4 pages.
de Caestecker et al., "Characterization of Functional Domains within Smad4/DPC4", *The Journal of Biological Chemistry*, vol. 272, No. 21, May 23, 1997, pp. 13690–13696.
Meersseman et al., "The C–terminal domain of Mad–like signal transducers is sufficient for biological activity in the Xenopus embryo and transcriptional activation", *Mechanisms of Development*, 61 (1997), pp. 127–140.
W. French Anderson. Human gene therapy. Nature, 392, S, 25–30, 1998.
Gencore DB Version 4.5 AC AB011141 US–09–449–285–1, 1998.
Gencore DB Version 4.5 AC Q14163 US–09–449–285–4, 1995.
Gencore DB Version 4.5 AC M89802 US–09–449–285–8, 1990.
Gencore DB Version 4.5 AC E10101 US–09–449–285–10, 1995.
PCT International Search Report, PCT/EP 98/03193, dated Nov. 27, 1998.
PCT International Preliminary Examination Report, PCT/EP 98/03193, dated Sep. 15, 1999.

* cited by examiner

*Primary Examiner*—Karen Cochrane Carlson
(74) *Attorney, Agent, or Firm*—TraskBritt

(57) ABSTRACT

The current invention concerns SMAD-interacting protein (s) obtainable by a two-hybrid screening assay whereby SMAD1 C-domain fused to GAL4 DNA-binding domain as "bait" and a cDNA library from mouse embryo as "prey" are used. Some characteristics of a specific SMAD-interacting protein (SIP1) of the family of zinc finger/homeodomain proteins including d-crystallin enhancer binding protein and/or *Drosophila* zfh-1 include an inability to interact with full-size XSMAD1 in yeast, $SIP1_{CZF}$ binds to E2 box sites, $SIP1_{CZF}$ binds to the Brachyury protein binding site and interferes with Brachyury-mediated transcription activation in cells and also interacts with the C-domain of SMAD 1, 2 and 5. The minimal length of the amino acid sequence necessary for binding with SMAD appears to be a 51 amino acid domain encompassing amino acids 166–216 of SEQ ID NO: 2 having the amino acid sequence as depicted in the one letter code: QHLGVGMEAPLLGFPTMNSNLSEVQKVL-QIVDNTVSRQKMDCKTEDISKLK (SEQ ID NO: 21).

8 Claims, 1 Drawing Sheet

SMAD-INTERACTING POLYPEPTIDES AND THEIR USE

CROSS-REFERENCE TO RELATED APPLICATIONS

This application is a divisional application of U.S. patent application Ser. No. 09/449,285, filed on 24 Nov. 1999, now U.S. Pat. No. 6,313,280, issued Nov. 6, 2001, which is a continuation of international patent application no. PCT/EP98/03193, filed on 28 May 1998, designating the United States of America, published in English Dec. 10, 1998, as international publication WO 98/55512.

REFERENCE TO A "SEQUENCE LISTING"

The computer readable form of the sequence listing in this application is identical with that filed in U.S. patent application Ser. No. 09/449,285, filed 24 Nov. 1999, now U.S. Pat. No. 6,313,280, issued Nov. 6, 2001. In accordance with 37 CFR § 1.821(e), please use the last-filed computer readable form filed in that application as the computer readable form for the instant application. The paper copy of the instant application is identical with the computer readable copy filed for application Ser. No. 09/449,285.

TECHNICAL FIELD

The present invention relates to SMAD—interacting polypeptides ("SIP's") such as cofactors for SMAD proteins and the use thereof.

BACKGROUND

The development from a single cell to a fully organized organism is a complex process wherein cell division and differentiation are involved. Certain proteins play a central role in this process. These proteins are divided into different families of which the transforming growth factor β ("TGF-β") family of ligands, their serine/threonine kinase ("STK") receptors and their signalling components are undoubtedly key regulatory polypeptides. Members of the TGF-b superfamily have been documented to play crucial roles in early developmental events such as mesoderm formation and gastrulation, but also at later stages in processes such as neurogenesis, organogenesis, apoptosis and establishment of left-right asymmetry. In addition, TGF-b ligands and components of their signal transduction pathway have been identified as putative tumor suppressors in the adult organism.

Recently, "SMAD proteins" have been identified as downstream targets of the STK receptors (Massagué, 1996, Cell, 85, p. 947–950). These SMAD proteins are signal transducers which become phosphorylated by activated type I receptors and thereupon accumulate in the nucleus where they may be involved in transcriptional activation. SMAD proteins comprise a family of at least 5 subgroups which show high cross-species homology. They are generally proteins of about 450 amino acids (50–60 kDa) with highly conserved N-terminal and C-terminal domains, linked by a variable, proline-rich, middle region. On the basis of experiments carried out in cell lines or in Xenopus embryos, it has been suggested that the subgroups define distinct signalling pathways: SMAD1 mediates BMP2/4 pathways, while SMAD2 and SMAD3 act in TGF-b/activin signal transduction cascades. It has been demonstrated that these SMADs act in a complex with SMAD4 (dpc-4) to elicit certain activin, bone morphogenetic protein (BMP) or TGF-b responses (Lagna et al., 1996, Nature, 383, p.832–836 and Zhang et al., 1996, Nature, 383, p.168–172).

SMAD proteins have a three-domain structure and their highly conserved carboxyl domain (C-domain) is necessary and sufficient for SMAD function in the nucleus. The concept that this domain of SMAD proteins might interact with transcription factors in order to regulate transcription of target genes has previously been put forth (Meersseman et al., 1997, Mech. Dev., 61, p.127–140). This hypothesis has been supported by the recent identification of a new winged-helix transcription factor ("FAST1") which forms an activin-dependent complex with SMAD2 and binds to an activin-responsive element in the Mix-2 promoter (Chen et al., Nature 383, p. 691–696, 1996). However, cofactors for SMAD proteins other than FAST 1 have not yet been identified.

Beyond the determination of the mechanism of activation of STK receptors and SMAD, and the heteromerization of the latter, little is known about other downstream components in the signal transduction machinery. Thus, understanding how cells respond to TGF-b related ligands remains a crucial central question in this field.

In order to clearly demonstrate that SMAD proteins might have a function in transcriptional regulation—either directly or indirectly—it is necessary to identify putative cofactors of SMAD proteins and response elements in target genes for these SMAD proteins and/or cofactors, and to investigate the ligand-dependency of these activities.

To understand those interactions, molecular and developmental biology research on (i) functional aspects of the ligands, receptors and signaling components (in particular, members of the SMAD family) in embryogenesis and disease, (ii) structure-function analysis of the ligands and the receptors, (iii) the elucidation of signal transduction, (iv) the identification of cofactors for SMAD (related) proteins, and (v) ligand-responsive genes in cultured cell and the Drosophila, amphibian, fish and murine embryo are all of utmost importance.

DISCLOSURE OF THE INVENTION

We have found that by carrying out a two-hybrid screening assay, SMAD-interacting protein(s) are obtainable where SMAD C-domain fused to a DNA-binding domain as "bait" and a vertebrate cDNA library as "prey" respectively are used. It is evident to those of skill in the art that other appropriate cDNA libraries can be used as well. By using, for example, SMAD1 C-domain fused to GAL4 DNA-binding domain and a mouse embryo cDNA as bait and prey respectively, a partial SMAD4 and other SMAD-interacting protein (SIP) cDNAs, including SIP1, were obtained.

Surprisingly, it has been found that at least four SMAD-interacting proteins thus obtained contain a DNA-binding zinc finger domain. One of these proteins, SIP 1, is a novel member of the family of zinc finger/homeodomain proteins containing d-crystallin enhancer binding protein and certain Drosophila zfh-1, the former of which has been identified as a DNA-binding repressor. It has been shown that one DNA-binding domain of SIP1 (the C-terminal zinc finger cluster or $SIP1_{CZF}$) binds to E2 box regulatory sequences and to the Brachyury protein binding site. It has been demonstrated in cells that SIP1 interferes with E2 box and Brachyury-mediated transcription activation. SIP1 fails to interact with full-size SMAD in yeast. We have shown for the first time that SMAD proteins can interact with a DNA-binding repressor and, as such, appear to be directly involved in TGF-B ligand-controlled repression of target genes which are involved in the strict regulation of normal early development.

In summary, characteristics of SIP 1 include the following:

a) it fails to interact with full-size XSMAD1 in yeast,
b) it is a new member of the family of zinc finger/homeodomain proteins including δ-crystallin enhancer binding protein and/or *Drosophila* zfh-1,
c) $SIP1_{CZF}$ binds to E2 box sites,
d) $SIP1_{CZF}$ binds to the Brachyury protein binding site,
e) it interferes with Brachyury-mediated transcription activation in cells, and
f) it interacts with the C-domain of SMAD 1, 2 and/or 5.

As used herein, "E2 box sites" means a -CACCTG-regulatory conserved nucleotide sequence which contains the binding site CACCT for δ-crystallin enhancer binding proteins as described in Sekido et al., 1996, *Gene*, 173, p.227–232. These E2 box sites are known targets for important basic helix-loop-helix (bHLH) factors such as MyoD, a transcription factor in embryogenesis and myogenesis.

So, the SIP1 according to the invention (a zinc finger/homeodomain protein) binds to specific sites in the promoter region of a number of genes which are relevant for the immune response and early embryogenesis and as such may be involved in transcriptional regulation of important differentiation genes in significant biological processes such as cell growth and differentiation, embryogenesis, and abnormal cell growth including cancer.

The invention also includes an isolated nucleic acid sequence including the nucleotide sequence as provided in SEQ ID NO: 1 coding for an SMAD-interacting protein or a functional fragment thereof.

Furthermore, a recombinant expression vector including the isolated nucleic acid sequence (in sense or anti-sense orientation) operably linked to a suitable control sequence belongs to the present invention and cells transfected or transduced with a recombinant expression vector as well.

Another aspect of the invention is a polypeptide including the amino acid sequence according to SEQ ID NO: 2 or a functional fragment thereof. The present invention also includes variants or homologues of amino acids enclosed in the disclosed polypeptides wherein the amino acids are modified and/or substituted by other amino acids obvious for a person skilled in the art. For example, post-expression modifications of the polypeptide such as phosphorylations are not excluded from the scope of the current invention.

A pharmaceutical composition including the previously identified nucleic acid(s) or a pharmaceutical composition including the polypeptide(s) are another aspect of the invention. The nucleic acid and/or polypeptide according to the invention can be optionally used for appropriate gene therapy purposes.

In addition, a method for diagnosing, prognosis and/or follow-up of a disease or disorder by using the nucleic acid(s) according to the invention or by using the polypeptide(s) also form an important aspect of the current invention. Furthermore, in the method for diagnosing, prognosis and/or follow-up of a disease or disorder, an antibody, directed against a polypeptide or fragment thereof according to the current invention, can also be conveniently used. As used herein, the term "antibody" refers, without limitation, to preferably purified polyclonal antibodies or monoclonal antibodies, altered antibodies, univalent antibodies, Fab proteins, single domain antibodies or chimeric antibodies. In many cases, the binding phenomenon of antibodies to antigens is equivalent to other ligand/anti-ligand binding.

A diagnostic kit including a nucleic acid(s) sequence and/or a polypeptide(s) or antibodies directed against the polypeptide or fragment thereof according to the invention for performing previously identified methods for diagnosing a disease or disorder clearly belong to the invention as well.

Diseases or disorders in this respect are, for instance, related to cancer, malformation, immune or neural diseases, or bone metabolism-related diseases or disorders. In addition, a disease affecting organs like skin, lung, kidney, pancreas, stomach, gonad, muscle or intestine can be diagnosed as well using the diagnostic kit according to the invention.

Using the nucleic acid sequences of the invention as a basis, oligomers of approximately 8 nucleotides or more can be prepared, either by excision or synthetically, which hybridize, for instance, with a sequence coding for SIP or a functional part thereof and are thus useful in identification of SIP in diseased individuals. These so-called "probes" are of a length which allows the detection of unique sequences of the compound to detect or determine by hybridization as defined above. While 6–8 nucleotides may be a workable length, sequences of about 10–12 nucleotides are preferred, and about 20 nucleotides appears optimal. The nucleotide sequence may be labelled, for example, with a radioactive compound, biotin, enzyme, dye stuff or metal sol, fluorescent or chemiluminescent compound. The probes can be packaged into diagnostic kits. Diagnostic kits include the probe nucleotide sequence, which may be labeled; alternatively, the probe may be unlabeled and the ingredients for labelling may be included in the kit in separate containers so that the probe can optionally be labeled. The kit may also contain other suitably packaged reagents and materials needed for the particular hybridization protocol, for example, standards, wash buffers, as well as instructions for conducting the test.

The diagnostic kit may include an antibody directed to a polypeptide or fragment thereof according to the invention in order to set up an immunoassay. Design of the immunoassay is subject to a great deal of variation, and the variety of these are known in the art. Immunoassays may be based, for example, upon competition, or direct reaction, or sandwich type assays.

An important aspect of the present invention is the development of a method of screening for compounds (chemically synthesized or available from natural sources) which affect the interaction between SMAD and SIP's having the current knowledge of the SMAD-interacting polypeptides (so-called SIP's such as SIP1 or SIP2 as specifically disclosed herein).

A transgenic animal harboring the nucleic acid(s) according to the invention in its genome also belongs to the scope of this invention. The transgenic animal can be used for testing medicaments and therapy models as well. As used herein, a transgenic animal means a non-human animal which has incorporated a foreign gene (called transgene) into its genome. Because this gene is present in germ line tissues, it is passed from parent to offspring, establishing lines of transgenic animals from a first founder animal. As such, transgenic animals are recognized as specific species variants or strains, following the introduction and integration of new gene(s) into their genome. The term "transgenic" has been extended to chimeric or "knockout" animals in which gene(s), or part of genes, have been selectively disrupted or removed from the host genome.

It will be appreciated that when a nucleic acid construct is introduced into an animal to make it transgenic, the nucleic acid may not necessarily remain in the form as introduced.

As used herein, "offspring" means any product of the mating of the transgenic animal whether or not with another transgenic animal, provided that the offspring carries the transgene.

Depending on the purpose of the gene transfer study, transgenes can be grouped into three main functional types: gain-of-function, reporter function and loss-of-function.

The gain-of-function transgenes are designed to add new functions to the transgenic individuals or to facilitate the identification of the transgenic individuals if the genes are expressed properly (including in some cell types only) in the transgenic individuals.

The reporter gene function is commonly used to identify the success of a gene transfer effort. Bacterial chloramphenicol acetyltransferase ("CAT"), b-galactosidase or luciferase genes fused to functional promoters represent one type of reporter function transgene.

The loss-of-function transgenes are constructed for interfering with the expression of host genes. These genes might encode an antisense RNA to interfere with the post-transcriptional process or translation of endogenous mRNAs. Alternatively, these genes might encode a catalytic RNA (a ribozyme) that can cleave specific mRNAs and thereby cancel the production of the normal gene product.

Optionally, loss of function transgenes can also be obtained by over-expression of dominant-negative variants that interfere with activity of the endogenous protein or by targeted inactivation of a gene, or parts of a gene, in which usually (at least a part of) the DNA is deleted and replaced with foreign DNA by homologous recombination. This foreign DNA usually contains an expression cassette for a selectable marker and/or reporter.

The invention also includes an SMAD-interacting protein characterized in that:
a) it interacts with full-size XSMAD1 in yeast,
b) it is a member of a family of proteins which contain a cluster of 5 CCCH-type zinc fingers including Drosophila "Clipper" and Zebrafish "No arches",
c) it binds single or double stranded DNA,
d) it has an RNAse activity, and
e) it interacts with the C-domain of SMAD 1, 2 and/or 5.

The invention also includes a method for post-transcriptional regulation of gene expression by members of the TGF-b superfamily by manipulation or modulation of the interaction between SMAD function and/or activity and mRNA stability.

DETAILED DESCRIPTION OF THE INVENTION

Figure 1:
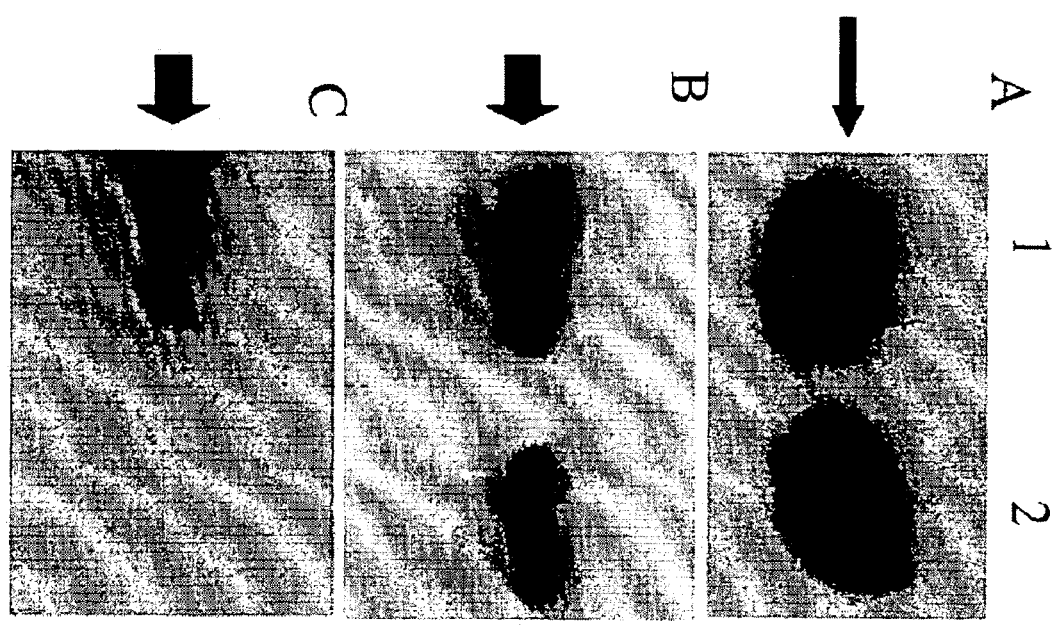
FIG. 1 shows that the XSMAD1 C-domain interacts with SIP1 in mammalian cells and deletion of the 51 amino acid ("aa") long SBD (SMAD binding domain) in SIP1 abolishes the interaction. COS-1 cells were transiently transfected with expression constructs encoding N-terminally myc-tagged SIP1 and a GST-XSMAD 1 C-domain fusion protein. The latter was purified from cell extracts using glutathione-sepharose beads. Purified proteins were visualized after SDS-PAGE and Western blotting using anti-GST antibody (Pharmacia), (Panel A, slim arrow). Myc-tagged SIP1 protein was co-purified with GST-XSMAD1 C-domain fusion protein, as was shown by Western blotting of the same material using anti-myc monoclonal antibody (Santa Cruz) (Panel C, lane one, thick arrow). Deletion of the 51 aa long SBD in SIP1 abolished this interaction (panel C, lane 2). Note that the amounts of purified GST-XSMAD1 C-domain protein and levels of expression of both SIP1 (wild type and SIP1 del SBD) proteins in total cell extracts were comparable (compare lanes 1 and 2 in panel A and B).

A two-hybrid screening assay for use with the invention may be performed as generally described by Chien et al., PNAS, 88, p.9578–9582 (1991).

The polypeptide or fragments thereof included within the invention are not necessarily translated from the nucleic acid sequence according to the invention but may be generated in any manner, including, for example, chemical synthesis or expression in a recombinant expression system. Generally, "polypeptide" refers to a polymer of amino acids, and does not refer to a specific length of the molecule. Thus, linear peptides, cyclic or branched peptides, peptides with non-natural or non-standard amino acids such as D-amino acids, ornithine and the like, oligopeptides and proteins are all included within the definition of polypeptide. The terms "protein" and "polypeptide", as used herein, are generally interchangeable. "Polypeptide" as previously mentioned refers to a polymer of amino acids (amino acid sequence) and does not refer to a specific length of the molecule. Thus, peptides and oligopeptides are included within the definition of polypeptide. This term also includes post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Control sequence", as used herein, refers to regulatory DNA sequences which are necessary to affect the expression of coding sequences to which they are ligated. The nature of such control sequences differs depending upon the host organism. In prokaryotes, control sequences generally include a promoter, ribosomal binding site, and terminators. In eukaryotes, generally control sequences include promoters, terminators and, in some instances, enhancers, transactivators, transcription factors or 5' and 3' untranslated cDNA sequences. The term "control sequence" is intended to include, at a minimum, all components, the presence of which are necessary for expression, and may also include additional advantageous components.

"Operably linked", as used herein, refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In the case where the control sequence is a promoter, it would be obvious to a skilled person to use double-stranded nucleic acid.

As used herein, "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

Furthermore, the current invention is not limited to the exact isolated nucleic acid sequences specifically identified herein, including the nucleotide sequence as mentioned in SEQ ID NO: 1, but also a nucleic acid sequence hybridizing to the nucleotide sequence as provided in SEQ ID NO: 1 or a functional part thereof and encoding an SMAD-interacting protein or a functional fragment thereof belongs to the present invention.

To clarify, as used herein, "hybridization" means conventional hybridization conditions known to the skilled person, preferably appropriate stringent hybridization conditions. Hybridization techniques for determining the complementarity of nucleic acid sequences are known in the art. The stringency of hybridization is determined by a number of factors during hybridization including temperature, ionic strength, length of time and composition of the hybridization buffer. These factors are outlined in, for example, Maniatis et al. (1982) *Molecular Cloning; A laboratory manual* (Cold Spring Harbor Press, Cold Spring Harbor, N.Y.).

The term "antigen" refers to a polypeptide or group of peptides which include at least one epitope. "Epitope" refers to an antibody binding site usually defined by a polypeptide including 3 amino acids in a spatial conformation which is unique to the epitope; generally an epitope consists of at least 5 such amino acids and more usually of at least 8–10 such amino acids.

The invention is further explained by the following illustrative EXAMPLES:

EXAMPLES

Example I
Yeast, Two-Hybrid Cloning of SMAD-Interacting Proteins

In order to identify cofactors for SMAD1, a two-hybrid screening in yeast was carried out using the XSMAD1 C-domain fused to GAL4 DNA-binding domain (GAL4 DBD) as bait, and a cDNA library from mouse embryo (12.5 dpc) as a source of candidate preys. The GAL4$_{DBD}$-SMAD1 bait protein failed to induce in the reporter yeast strain GAL4-dependent HIS3 and LacZ transcription on its own or in conjunction with an empty prey plasmid. Screening of 4 million yeast transformants identified about 500 colonies expressing HIS3 and LacZ. The colonies displaying a phenotype, which was dependent on expression of both the prey and the bait cDNAs, were then characterized. Plasmids were rescued and the prey cDNAs sequenced (SEQ ID NOS: 1–20 of the Sequence Listing enclosed; for each nucleic acid sequence only one strand is depicted in the Listing). Four of these (th1, th12, th76 and th74 respectively also denominated in this application as SIP1, SIP2, SIP5 and SIP7 respectively) are disclosed in detail (embedded in SEQ ID NOS: 1, 2, 3, 4, 10, and 8 respectively). One (th72= combined SEQ ID NO: 6 and 7) encodes a protein in which the GAL4 transactivation domain (GAL4$_{TAD}$) is fused in-frame to a partial SMAD4 cDNA, which starts at amino acid (aa) 252 in the proline-rich domain. SMAD4 has been shown to interact with other SMAD proteins, but no SMAD has been picked-up thus far in a two-hybrid screen in yeast, using the C-domain of another SMAD as bait. These data suggest that the N-domain of both interacting SMAD proteins, as well as part of (SMAD4) or the entire (SMAD1) proline-rich domain, is dispensable for heterodimeric interaction between SMAD proteins, at least when using a two-hybrid assay in yeast.

The cDNA insert of the second positive prey plasmid, th1 (embedded in SEQ ID NO: 1), encodes a protein in which the GAL4$_{TAD}$-coding sequence is fused in-frame to about a 1.9 kb-long th1 cDNA, which encodes a polypeptide SIP1 (Th1) of 626 aa. Database searches revealed that SIP1 (Th1) contained a homeodomain-like segment, and represents a novel member of a family of DNA-binding proteins including vertebrate d-crystallin enhancer binding proteins (d-EF1) and *Drosophila* zfh-1. These zinc finger/homeodomain-containing transcription factors are involved in organogenesis in mesodermal tissues and/or development of the nervous system. The protein encoded by th1 cDNA is an SMAD-interacting protein (SIP) and was named SIP1 (TH1).

Example II
SIP1
Characterization of SIP1-SMAD Interaction in Yeast and In Vitro The binding of SIP1 (TH1) to full-size XSMAD1 and modified C-domains was tested. The latter have either an amino acid substitution (G418S) or a deletion of the last 43 aa (D424-466). The first renders the SMAD homolog in *Drosophila* Mad inactive and abolishes BMP-dependent phosphorylation of SMAD1 in mammalian cells. A truncated Mad, similar to mutant D424-466, causes mutant phenotypes in *Drosophila*, while a similar truncation in SMAD4 (dpc-4) in a loss-of-heterozygosity background is associated with pancreatic carcinomas. SIP1 (TH1) neither interacts with full-size XSMAD1 nor, interacts with mutant D424-466. The absence of any detectable association of full-size XSMAD1 was not due to inefficient expression of the latter in yeast, since one other SMAD-interacting prey (th12) efficiently interacted with the full-length SMAD bait. Lack of association of SIP1 (TH1) with full-size XSMAD1 in yeast follows previous suggestions that the activity of the SMAD C-domain is repressed by the N-domain, and that this repression is eliminated in mammalian cells by incoming BMP signals. The G418S mutation in the C-domain of SMAD 1 does not abolish interaction with SIP1, suggesting that this mutation affects another aspect of SMAD1 function. The ability of the full-size G418S SMAD protein to become functional by activated receptor STK activity may thus be affected, but not the ability of the G418S C-domain to interact with downstream targets. This indicates that activation of SMAD is a prerequisite for and precedes interaction with targets such as SIP1. The deletion in mutant D424-466 includes three conserved and functionally important serines at the C-terminus of SMAD which are direct targets for phosphorylation by the activated type I STK receptor.

The C-domains of SMAD1 and SMAD2 induce ventral or dorsal mesoderm, respectively, when over-expressed individually in *Xenopus* embryos, despite their very high degree of sequence conservation. Very recently, SMAD5 has been shown to induce ventral fates in the *Xenopus* embryo. To investigate whether the striking differences in biological activity of SMAD1, -5 and SMAD2 could be due to distinct interactions with cofactors, the ability of SIP1 (TH1) protein to interact with the C-domains of SMAD1, -5 and SMAD2 in a yeast two-hybrid assay was tested. SIP1 (TH1) was found to interact in yeast with the C-domain of all three SMAD members. Then the interaction of SIP1 with different SMAD C-domains in vitro was investigated, using glutathione-S-transferase ("GST") pull-down assays. GST-SMAD fusion proteins were produced in *E. Coli* and coupled to glutathione-sepharose beads. An unrelated GST fusion protein and unfused GST were used as negative controls. Radio-labeled, epitope-tagged SIP1 protein was successfully produced in mammalian cells using a vaccinia virus (T7VV)-based system. Using GST-SMAD beads, this SIP1 protein was pulled down from cell lysates, and its identity was confirmed by Western blotting. Again, as in yeast, it was found that SIP1 is a common binding protein for different SMAD C-domains, suggesting that SIP1 might mediate common responses of cells to different members of the TGF-β superfamily. Alternatively, SMAD proteins may have different affinities for SIP1 in vivo, or other mechanisms might determine the specificity, if any, of SMAD-SIP1 interaction.

Example III

SIP1 is a New Member of Zinc Finger/Homeodomain Proteins of the d-EF1 Family

Additional SIP1 open reading frame sequences were obtained by a combination of cDNA library screening with 5'RACE-PCR. The screening yielded a 3.2 kb-long SIP1 cDNA (tw6), which overlaps partially with th1 cDNA. The open reading frame of SIP1 protein encodes 944 aa (SEQ ID NO: 2), and showed homology to certain regions in d-EF1, ZEB, AREB6, BZP and zfh-1 proteins, and strikingly similar organization of putative functional domains. Like these proteins, SIP1 contains two zinc finger clusters separated by a homeodomain and a glutamic acid-rich domain. Detailed comparisons reveal that SIP1 is a novel and divergent member of the two-handed zinc finger/homeodomain proteins. As in d-EF1, three of the five residues that are conserved in helix 3 and 4 of all canonical homeodomains are not present in SIP1. SIP1 (Th1) which contains the homeodomain but lacks the C-terminal zinc finger cluster and glutamic acid-rich sequence, interacts with SMAD. This interaction is maintained upon removal of the homeodomain-like domain, indicating that a segment encoding aa 44-236 of SIP1 (numbering according to SEQ ID NO: 2) is sufficient for interaction with SMAD. To narrow this domain further down, progressive deletion mutants, starting from the N-terminus, as well as the C-terminus of this 193 aa region were made. Progressive 20 aa deletion constructs were generated by PCR. Two restriction sites (5' end SmaI site, 3' end XhoI site) were built in to allow cloning of amplified sequences in the yeast two-hybrid bait vector pACT2 (Clontech). An extensive two-hybrid experiment was performed with these so-called SBD mutant constructs as a prey and the XSMAD1 C-domain as bait. The mutant SBD constructs that encoded aa 166-236 (of SEQ ID NO: 2) or aa 44-216 were still able to interact with the bait plasmid, whereas mutant constructs encoding aa 186-236 or aa 44-196 could not interact with the bait. In this way, the smallest domain that still interacts with the XSMAD1 C-domain was defined as a 51 aa domain encompassing aa 166-216 of SEQ ID NO: 2.

The amino acid sequence of the SBD, necessary for the interaction with SMAD, thus is (depicted in one-letter code): QHLGVGMEAPLLGFPTMNSNLSEVQKVL-QIVDNTVSRQKMDCKTEDISKLK (SEQ ID NO: 21).

Deletion of an additional 20 aa at the N- or C-terminal end of this region disrupted the SMAD binding activity. Subsequently, this 51 aa region was deleted in the context of SIP1 protein, again using a PCR-based approach, generating an NcoI restriction site at the position of the deletion. This SIP 1DSBD51 was not able to interact with the SMAD C-domain any longer, as assayed by a "mammalian pull-down assay". In these experiments, SIP1, myc-tagged at its N-terminal end, was expressed in COS-1 cells together with a GST-XSMAD1 C-domain fusion protein. Myc-SIP1 protein was co-purified from cell extracts with the GST-XSMAD1 C-domain fusion protein using glutathione-sepharose beads, as was demonstrated by Western blotting using anti-myc antibody. Deletion of the 51 aa in SIP1 abolished the interaction, as detected in this assay, with the XSMAD1 C-domain. (See, FIG. 1).

Example IV

Analysis of the DNA-Binding Activity of the C-Terminal Zinc Finger Cluster of SIP1.

d-EF1 is a repressor that regulates the enhancer activity of certain genes. This repressor binds to the E2 box sequence (5'-CACCTG) which is also a binding site for a subgroup of basic helix-loop-helix (bHLH) activators (Sekido et al., 1994, Mol. Cell. Biol., 14, p. 5692–5700). Interestingly, the CACCT sequence which has been shown to bind d-EF1 is also part of the consensus binding site for Bra protein. It has been proposed that cell type-specific gene expression is accomplished by competitive binding to CACCT sequences between repressors and activators. δ-EF1 mediated repression could be the primary mechanism for silencing the IgH enhancer in non-B cells. d-EF1 is also present in B-cells, but is counteracted by E2A, a bHLH factor specific for B-cells. Similarly, d-EF1 represses the Igk enhancer where it competes for binding with bHLH factor E47.

The C-terminal zinc finger cluster of d-EF1 is responsible for binding to E2 box sequences and for competition with activators. Considering the high sequence similarities in this region between SIP1 and d-EF1, it was decided to test first whether both proteins have similar DNA binding specificities, using gel retardation assays. Therefore, the DNA-binding properties of the C-terminal zinc finger cluster of SIP1 (named SIP1$_{CZF}$) was analyzed. SIP1$_{CZF}$ was efficiently produced in and purified from E. coli as a short GST fusion protein. Larger GST-SIP1 fusion proteins were subject to proteolytic degradation in E. coli.

Purified GST-SIP1$_{CZF}$ was shown to bind to the E2 box of the IgH kE2 enhancer. A mutation of this site (Mut1), which was shown previously to affect the binding of the bHLH factor E47 but not d-EF1, did not affect binding of SIP1$_{CZF}$. Two other mutations in this kE2 site (Mut2 and Mut4, respectively) have been shown to abolish binding of d-EF1 (Sekido et al., 1994) and did so in the case of SIP1$_{CZF}$. In addition, also the binding of SIP1$_{CZF}$ to the Nil-2A binding site of the interleukin-2 promoter, the Bra protein binding site and the AREB6 binding site were demonstrated. The specificity of the binding of SIP1$_{CZF}$ to the Bra binding site was further demonstrated in competition experiments. Binding of SIP1$_{CZF}$ to this site was competed by excess unlabeled Bra binding site probe, while kE2 wild type probe competes, albeit less efficiently than its variant Mut1, which is a very strong competitor. kE2-Mut2 and kE2-Mut4 failed to compete, as did the GATA-2 probe, while the AREB6 site competed very efficiently. From these experiments, it can be concluded that GST-SIP1$_{CZF}$ fusion protein displays the same DNA binding specificity as other GST fusion proteins made with the CZF region of d-EF1 and related proteins (Sekido et al., 1994). In addition, it was demonstrated for the first time that SIP 1 binds specifically to regulatory sequences that are also target sites for Bra. This may be the case for the other d-EF1-related proteins as well and these may interfere with Bra-dependent gene activation in vivo.

Analyses were done to sites recognized by the bHLH factor MyoD. MyoD has been shown to activate transcription from the muscle creatine kinase ("MCK") promoter by binding to E2 box sequences (Weintraub et al., 1994, Genes Dev., 8, p.2203–2211; Katagiri et al., 1997, Exp. Cell Res. 230, p. 342–3 51). Interestingly, d-EF1 has also been demonstrated to repress MyoD-dependent activation of the MCK enhancer, as well as myogenesis in 10T½ cells, and this is thought to involve E2 boxes (Sekido et al., 1994). In addition, TGF-B and BMP-2 have been reported to down-regulate the activity of muscle-specific promoters, and this inhibitory effect is mediated by E2 boxes (Katagiri et al., 1997). The latter are present in the regulatory regions of many muscle-specific genes, are required for muscle-specific expression, and are optimally recognized by heterodimers between myogenic bHLH proteins (of the MyoD family) and of widely expressed factors like E47. $SIP1_{CZF}$ was able to bind to a probe that encompasses the MCK enhancer E2 box and this complex was competed by the E2 box oligonucleotide and by other SIP1 binding sites. In addition, a point mutation within this E2 box that is similar to the previously used kE2-Mut4 site also abolished binding of $SIP1_{CZF}$. These results confirm that $SIP1_{CZF}$ binds to the E2 box of the MCK promoter. SIP1, as SMAD-interacting and MCK E2 box binding protein, may therefore represent the factor that mediates the TGF-β and BMP repression of the MyoD-regulated MCK promoter (Katagiri et al., 1997).

Example V
SIP1 is a BMP-Dependent Repressor of Bra Activator

The experiments have demonstrated that $SIP1_{CZF}$ binds to the Bra protein binding site, to IL-2 promoter, and to E2 boxes, the latter being implicated in BMP or TGF-δ-mediated repression of muscle-specific genes. These observations prompted therefore to test whether SIP1 (as $SIP1_{TW6}$) is a BMP-regulated repressor. A reporter plasmid containing an SIP1 binding site (the Bra protein binding site) fused to the luciferase gene was constructed. COS cells, maintained in low serum (0.2%) medium during the transfection, were used in subsequent transient transfection experiments since they have been documented to express BMP receptors and support signalling (Hoodless et al., 1996, Cell, 85, p.489–500). It was found in the experiment that $SIP1_{TW6}$ is not able to change the transactivation activity of Bra protein via the Bra binding site. In addition, no transactivation of this reporter plasmid by $SIP1_{TW6}$ could be detected in the presence of 10% or 0.2% serum, and in the absence of Bra expression vector.

Therefore, identical experiments were carried out in which the cells were exposed to BMP-4. $SIP1_{TW6}$ repressed the Bra-mediated activation of the reporter. It does this in a dose-dependent fashion (amount of $SIP1_{TW6}$ plasmid, concentration of BMP4). Total repression has not been obtained in this type of experiment, because the transfected COS cells were exposed only after 24 hours to BMP-4. Consequently, luciferase mRNA and protein accumulate during the first 24 hours of the experiment as the result of Brachyury activity. The conclusion from these experiments clearly shows that SIP1 is a repressor of Bra activator, and its activity as repressor is detected only in the presence of BMP. It is important that SIP1 has not been found to be an activator of transcription via Bra target sites. This is interesting, since the presence in d-EF1-like proteins of a polyglutamic acid-rich stretch (which is also present in $SIP1_{TW6}$ used here) has led previously to the speculation that these repressors might act as transcriptional activators as well. In particular, AREB6 has been shown to bind to the promoter of the housekeeping gene Na,K- ATPase a-1 and to repress gene expression dependent on cell type and on the context of the binding site (Watanabe et al., 1993, *J. Biochem.*, 114, p. 849–855).

Example VI
SIP1 mRNA Expression in Mice

Northern analysis demonstrated the presence of a major SIP1 6 kb mRNA in the embryo and several tissues of adult mice, with very weak expression in liver and testis. A minor 9 kb-long transcript is also detected, which is, however, present in the 7 dpc embryo. In situ hybridization documented SIP1 transcription in the 7.5 dpc embryo in the extra-embryonic and embryonic mesoderm. The gene is weakly expressed in embryonic ectoderm. In the 8.5 dpc embryo, very strong expression is seen in extra-embryonic mesoderm (blood islands), neuroepithelium and neural tube, the first and second branchial arches, the optic eminence, and predominantly posterior presomitic mesoderm. Weaker but significant expression is detected in somites and notochord. Between day 8.5 and 9.5, this pattern extends clearly to the trigeminal and facio-acoustic neural crest tissue. Around mid-gestation, the SIP1 gene is expressed in the dorsal root ganglia, spinal cord, trigeminal ganglion, the ventricular zone of the frontal cortex, kidney mesenchyme, non-epithelial cells of duodenum and mid-gut, pancreatic primordium, urogenital ridge and gonads, the lower jaw and the snout region, cartilage primordium in the humerus region, the primordium of the clavicle and the segmental pre-cartilage sclerotome-derived condensations along the vertebral axis. SIP1 mRNA can also be detected in the palatal shelf, lung mesenchyme, stomach and inferior ganglion of the vagus nerve. In addition, primer extension analysis has demonstrated the presence of SIP1 mRNA in embryonic stem cells. It is striking that the expression of SIP1 in the 8.5 dpc embryo in the blood islands and presomitic mesoderm coincides with tissues affected in BMP-4 knockout mice, which have been shown to die between 6.5 and 9.5 dpc with a variable phenotype. These surviving till later stages of development showed disorganized posterior structures and a reduction in extra-embryonic mesoderm, including blood islands (Winnier et al., 1995, *Genes Dev.*, 9, 2105–2116).

The mRNA expression of d-EF1 proteins has been documented as well. In mouse, d-EF1 mRNA has been detected in mesodermal tissues such as notochord, somites and nephrotomes, and in other sites such as the nervous system and the lens in the embryo (Funahashi et al., 1993, Development, 119, p.433–446). In adult hamster, d-EF1 mRNA has been detected in the cells of the endocrine pancreas, anterior pituitary and central nervous system (Franklin et al., 1994, *Mol. Cell Biol.*, 14, p. 6773–6788). The majority of these d-EF1 and SIP1 expression sites overlap with sites where the restricted expression pattern of certain type I STK receptors (such as ALK-4/ActR-IA, and ALK-6/BMPR-IB) has been documented (Verschueren et al., 1995, Mech. Dev., 52, p.109–123).

Example VII
SIP2
Characterization of SIP2

SIP2 was picked up initially as a two-hybrid clone of 1052 base pairs ("bp") (th12) that shows interaction in yeast with SMAD1, 2 and 5 C-terminal domains and full-size SMAD1. Using GST pull-down experiments (as described for SIP1), also an interaction with SMAD1, 2 and 5 C-terminal domains in vitro have been demonstrated.

a) SIP2 Full-Length Sequence

Th12 showed high homology to a partial cDNA (KIAA0150) isolated from the human myoblast cell line KG1. However, this human cDNA is +/−2 kb longer at the 3' end of th 12. Using this human cDNA, an EST library was screened and mouse EST were detected homologous to the 3' end of KIAA0150 cDNA. Primers were designed based on th12 sequence and the mouse EST found to amplify a cDNA that contains the stop codon at the 3'end. 5' sequences encompassing the start codon was obtained using 5'RACE-PCR.

Gene bank accession numbers for the mentioned EST clones used to complete the SIP2 open reading frame: Human KIAA0150; D63484 and Mouse EST sequence; Soares mouse p3NWF19.5; W82188.

Primers used to reconstitute SIP2 open reading frame: based on th12 sequence: F3th12F (forward primer) 5'-cggcggcagatacgcctcctgca (SEQ ID NO: 22) based on EST sequence: th12mouse1 (reverse primer) 5'-caggagcagttgtgggtagagccttcatc (SEQ ID NO: 23).

Primers used for 5'-race; all are reverse primers derived from th12 sequence 1:5'-ctggactgagctggacctgtctctccagtac (SEQ ID NO: 24) 2:5'-cacaagggagtatttcttgcgccacgaagg (SEQ ID NO: 25) 3:5'-gccatggtgtgaggagaagc (SEQ ID NO: 26).

The full-size SIP2 deduced from the assembly of these sequences contains 950 amino acids as depicted in SEQ ID NO. 4, while the nucleotide sequence is depicted in SEQ ID NO. 3.

b) SIP2 Sequence Homologies

SIP2 contains a domain encompassing 5 CCCH-type zinc fingers. This domain was found in other protein such as Clipper in *Drosophila*, No Arches in Zebrafish and CPSF in mammals. No Arches is essential for development of the branchial arches in Zebrafish and CPSF is involved in transcription termination and polyadenylation. The domain containing the 5 CCCH in Clipper was shown to have an EndoRNAse activity (see below).

c) SIP2 CCCH Domain has an RNAse Activity

The domain containing the 5 CCCH-type zinc fingers of SIP2 was fused to GST and the fusion protein was purified from *E coli*. This fusion protein displays an RNAse activity when incubated with labelled RNA produced in vitro. In addition, it has been shown that this fusion protein was able to bind single-stranded DNA.

In more detail, GST fusion proteins of SIP2 5xCCCH; PLAG1 (an unrelated zinc finger protein), $SIP1_{CZF}$ (C-terminal zinc finger cluster of SIP1) and th1 (SIP1 partial polypeptide isolated in the two-hybrid screening), and the cytoplasmatic tail of CD40 were produced in *E. coli* and purified using glutathione-sepharose beads. Three $^{35}S$ labelled substrates, previously used to demonstrate the RNAse activity of Clipper, a related protein from *Drosophila* (Bai, C. and Tolias P.P. 1996, cleavage of RNA Hairpins Mediated by a Developmentally Regulated CCCH Zinc Finger Protein. *Mol Cell Biol* 16: 6661–6667) were produced by in vitro transcription. The RNA cleavage reactions with purified GST fusion proteins were performed in the presence of RNAsin (blocking RNAseA activity). Equal aliquots of each reaction were taken out at time points 1', 7', 15', 30', 60'. Degradation products were separated on a denaturing polyacrylamide gel and visualized by autoradiography. These experiments demonstrated that GST-SIP2 5XCCCH has an RNAse activity and degrades all tested substrates, while GST-PLAG1, GST-CD40, GST-SIP1$_{CZF}$ and GST-th1 do not have this activity.

Interaction between th12 (partial SIP2 polypeptide) and SMAD C-domains in GST pull-down experiments.

C-domains of *Xenopus* (X)SMAD1 and mouse SMAD2 and 5 were produced in *E. coli* as fusion proteins with glutathione-S-transferase and coupled to glutathione beads. An unrelated GST-fusion protein (GST-CD40 cytoplasmatic mail) and GST itself were used as negative controls.

Th12 protein, provided with an HA-tag at its N-terminal end, was produced in Hela cells using the T7 vaccinia virus expression system and metabolically labelled. Expression of th12 was confirmed by immune precipitation with HA antibody, followed by SDS-page and autoradiography. Th12 protein is produced as a ±50 kd protein. Cell extracts prepared from Hela cells expressing this protein were mixed with GST-SMAD C-domain beads in GST pull-down buffer and incubated overnight at 4° C. The beads were then washed four times in the same buffer, the bound proteins eluted in Laemmli sample buffer and separated by SDS-PAGE. "Pulled down" th12 protein was visualized by Western blotting, using HA antibody. These experiments demonstrate that th12 is efficiently pulled down by GST-SMAD C-domain beads, and not by GST-CD40 or GST alone.

Conclusion on SIP2

SIP2 is a SMAD-interacting protein that contains an RNAse activity. The finding that SMADs interact with potential RNAses provides an unexpected link between the TGF-b signal transduction and mRNA stabilization.

Example VIII

SIP5

Characterization of SIP5

One contiguous open reading frame is fused in frame to the GAL4 transactivating domain in the two-hybrid vector pACT-2 (Clontech). This represents a partial cDNA, since no in-frame translational stop codon is present. The sequence has no significant homology to anything in the database, but displays a region of high homology with the following EST clones:

Mouse: accession numbers: AA212269 (Stratagene mouse melanoma); AA215020 (Stratagene mouse melanoma), AA794832 (Knowles Solter mouse 2 c) and Human: accession numbers AA830033, AA827054, AA687275, AA505145, AA371063.

Analysis of interaction of the SIP5 prey protein with different bait proteins (which are-described in the data section obtained with SIP1) in a yeast two-hybrid assay is as follows:

| | |
|---|---|
| Empty bait vector pGBT9 | – |
| Full-length XSMAD1 | + |
| XSMAD1 C-domain | + |
| XSMAD1 C-domain with G418S substitution | + |
| Mouse SMAD2 C-domain | + |
| Mouse SMAD5 C-domain | + |
| Lamin (pLAM; Clontech) | – |

SIP5 partial protein encoded by the above-described cDNA also interacts with XSMAD1, mouse SMAD2 and 5 C-domains in vitro as analyzed by the GST pull-down assay (previously described for SIP1 and SIP2). Briefly, the partial SIP5 protein was tagged with a myc tag at its C-terminal end and expressed in COS-1 cells. GST-SMAD C-domain fusion proteins, GST-CD40 cytoplasmatic tail and GST alone were expressed in *E. coli* and coupled to glutathione-sepharose beads. These beads were subsequently used to pull down partial SIP5 protein from COS cell lysates, as was demonstrated after SDS-PAGE of pulled down proteins followed by Western blotting using anti-myc antibody. In this assay, SIP5 was pulled down by GST-XSMAD1, 2 and 5 C-domains, but not by GST alone or GST-CD40. A partial, but coding, nucleic acid sequence for SIP5 is depicted in SEQ ID NO: 10.

Example IX

SIP7 (Characterization of SIP7)

One contiguous open reading frame is fused in frame to the GAL4 transactivating domain in the two-hybrid vector pACT2. This is a partial clone, since no in-frame translational stop codon is present. Part of this clone shows homology to Wnt-7b, accession number: M89802, but the clone seems to be a novel cDNA or a cloning artefact. The homology of the SIP7 cDNA with the known Wnt7-b cDNA starts at nucleotide 390 and extends to nucleotide 846. This corresponds to the nucleotides 74–530 in Wnt7-b coding sequences (with A of the translational start codon considered as nucleotide nr 1). In SIP7 cDNA, this region of homology is preceded by a sequence that shows no homology to anything in the database. It is not clear whether the SIP7 cDNA is, for example, a new Wnt7-b transcript or whether it is a scrambled clone as a result of the fusion of two cDNAs during generation of the cDNA library.

Analysis of the interaction of the SIP7 prey protein with different bait proteins in a yeast two-hybrid assay can be summarized as follows:

| | |
|---|---|
| PGBT9 | − |
| Full-length XSMAD1 | − |
| XSMAD1 C-domain | + |
| XSMAD1 C-domain, G418S | + |
| XSMAD1 C-domain del aa 424–466 | − |
| XSMAD1 N-terminal domain | − |
| Mouse SMAD2 C-domain | + |
| Mouse SMAD5 C-domain | + |
| Lamin (pLAM) | − |

SIP7 partial protein encoded by the above-described cDNA also interacts with XSMAD1, mouse SMAD2 and 5 C-domains in vitro as analyzed by the GST pull-down assay, as described above for SIP5. In this assay, N-terminally myc-tagged SIP7 protein was specifically pulled down by GST-XSMAD1, 2 and 5 C-domains, but not by GSTalone or GST-CD40. A partial, but coding, nucleic acid sequence for SIP7 is depicted in SEQ ID NO: 8.

SIP7 partial protein encoded by above described cDNA also interacts with XSMAD1, mouse SMAD2 and 5 C-domains in vitro as analysed by the GST pull down assay, as described above for SIP5. In this assay, N-terminally myc-tagged SIP7 protein was specifically pulled down by GST-XSMAD1, 2 and 5 C-domains, but not by GSTalone or GST-CD40. A partial, but coding, nucleic acid sequence for SIP7 is depicted in SEQ ID NO: 8.

General Description of the Methods Used

Plasmids and DNA Manipulations

Mouse SMAD1 and SMAD2 cDNAs used in this study were identified by low stringency screening of oligo-dT primed 1Exlox cDNA library made from 12 dpc mouse embryos (Novagen), using SMAD5 (MLP1.2 clone as described in Meersseman et al., 1997, Mech. Dev., 61, p.127–140) as a probe. The same library was used to screen for full-size SIP1, and yielded 1ExTW6. The tw6 cDNA was 3.6 kb long, and overlapped with th1 cDNA, but contained additional 3'-coding sequences including an in-frame stop codon. Additional 5' sequences were obtained by 5' RACE using the Gibco-BRL 5' RACE kit.

XSMAD1 full-size and C-domain bait plasmids were constructed using previously described EcoRI-XhoI inserts (Meersseman et al., 1997, Mech. Dev., 61, p.127–140), and cloned between the EcoRI and SalI sites of the bait vector pGBT-9 (Clontech), such that in-frame fusions with GAL4$_{DBD}$ were obtained. Similar bait plasmids with mouse SMAD1, SMAD2 and SMAD5 were generated by amplifying the respective cDNA fragments encoding the C-domain using Pfu polymerase (Stratagene) and primers with EcoRI and XhoI sites. The G418S XSMAD1 C-domain was generated by oligonucleotide-directed mutagenesis (Biorad).

To generate in-frame fusions of SMAD C-domains with GST, the same SMAD fragments were cloned in pGEX-5X-1 (Pharmacia). The phage T7 promoter-based SIP1 (TH1) construct for use in the T7VV system was generated by partial restriction of the th1 prey cDNA with BglII, followed by restriction with SalI such that SIP1 (TH 1) was lifted out of the prey vector along with an in-frame translational start codon, an HA-epitope tag of the flu virus, and a stop codon. This fragment was cloned into pGEM-3Z (Promega) for use in the T7VV system. A similar strategy was used to clone SIP2 (th12) into pGEM-3Z.

PolyA$^{30}$ RNA from 12.5 dpc mouse embryos was obtained with OLIGOTEX-dT (Qiagen). Randomly primed cDNA was prepared using the SUPERSCRIPT CHOICE SYSTEM (Gibco-BRL). cDNA was ligated to an excess of Sfi double-stranded adaptors containing StuI and BamHI sites. To facilitate cloning of the cDNAs, the prey plasmid pAct (Clontech) was modified to generate pAct/Sfi—Sfi. Restriction of this plasmid with Sfi generates sticky ends which are not complementary, such that self-ligation of the vector is prevented upon cDNA cloning. A library containing 3.6×10$^6$ independent recombinant clones with an average insert size of 1,100 bp was obtained.

Synthesis of SIP1 and GST Pull-Down Experiments

Expression of SIP1 (TH1) and SIP2 (TH12) in mammalian cells with the T7VV system and the operation of the cell lysates were as described previously (Verschueren, K. et al., 1995, Mech. Dev., 52, p.109–123).

GST fusion proteins were expressed in E. coli (strain BL21) and purified on glutathione-sepharose beads (Pharmacia). The beads were washed first four times with PBS supplemented with protease inhibitors, and then mixed with 50 µl of lysate (prepared from T7VV-infected SIP1-expressing mammalian cells) in 1 ml of GST buffer (50 mM Tris-HCl pH 7.5, 120 mM NaCl, 2 mM EDTA, 0.1% (v/v) NP-40, and protease inhibitors). They were mixed at 4° C. for 16 hours. Unbound proteins were removed by washing the beads four times with GST buffer. Bound proteins were harvested by boiling in sample buffer and resolved by SDS-PAGE. Separated proteins were visualized using autoradiography or immunodetection after Western blotting using anti-HA monoclonal antibody (12CA5) and alkaline phosphatase-conjugated anti-mouse 2ary antibody (Amersham).

EMSA (Electrophoretic Mobility Shift Assay)

The sequence of the kE2 WT and mutated kE2 oligonucleotides are identical as disclosed in Sekido do et al. (1994, Mol. Cell Biol., 14, p. 5692–5700). The sequence of the AREB6 oligonucleotide was obtained from Ikeda et al. (1995, Eur. J. Biochem, 233, p. 73–82). IL2 oligonucleotide is depicted in Williams et al. (1991, Science, 254, p. 1791–1794).

The sequence of Brachyury binding site is 5'-TGACACCTAGGTGTGAATT-3' (SEQ. ID. NO: 27). The negative control GATA2 oligonucleotide sequences originated from the endothelin promoter (Dorfman et al. 1992, J. Biol. Chem., 267, p. 1279–1285). Double-stranded oligonucleotides were labelled with polynucleotide kinase and $^{32}$P g-ATP and purified from a 15% polyacrylamide gel. Gel retardation assays were performed according to Sekido et al. (1994, Mol. Cell Biol., 14, p. 5692–5700).

RESULTS OF TWO-HYBRID SCREENING (XSMAD1 C-domain bait versus 12.5 dpc mouse embryo library; 600,000 recombinant clones screened in 4×10$^6$ yeasts.

SIP 1

Three independent clones isolated (th1, th88 and th94)

Zinc-finger-homeodomain protein

Homology to d-EF1 (see above)
Interactions in yeast:

| | |
|---|---|
| XSMAD1 C-domain bait | + |
| Empty bait | − |
| Lamin | − |
| XSMAD1 full-length | − |
| XSMAD1 N-domain | − |
| mSMAD1 C-domain | + |
| mSMAD2 C-domain | + |
| mSMAD5 C-domain | + |
| XSMAD1 C-domain del 424–466 | − |
| XSMAD1 C-domain G418S | + |

Interaction with C-domain of XSMAD1 and mSMADs confirmed in vitro using GST pull-downs and co-immunoprecipitations
Extended clone (TW6) isolated through library screening using th1 sequences as a probe
C-terminal TW6 zinc-finger cluster binds to E2 box sequences (cfr dEF-1), Brachyury T binding site, Brachyury promoter sequences SIP2 (also called clone TH12)— Three independent clones isolated (th 12, th73, th93)
    Highly homologous to KIAA0150 gene product, isolated from the myeloblast cell line KG1(Ref: Nagase et al. 1995; *DNA Res* 2 (4) 167–174.
Interactions in yeast:

| | |
|---|---|
| XSMAD1 C-domain bait | + |
| Empty bait | − |
| Lamin | − |
| XSMAD1 full-length | + |
| XSMAD1 N-domain | ND |
| mSMAD1 C-domain | + |
| mSMAD2 C-domain | + |
| mSMAD5 C-domain | + |
| XSMAD1 C-domain del 424–466 | − |
| XSMAD1 C-domain G418S | + |

TH60
Two independent clones isolated (th60 and th77)
Zinc finger protein
    homology to snail (transcriptional repressor) and to ATBF1 (complex homeodomain zinc finger protein)
Interactions in yeast:

| | |
|---|---|
| XSMAD1 C-domain bait | + |
| Empty bait | − |
| Lamin | − |

TH72
One clone isolated
Encodes a partial DPC-4 (SMAD4) cDNA (see above)
Interactions in yeast:

| | |
|---|---|
| XSMAD1 C-domain bait | +++ |
| Empty bait | − |
| Lamin | − |
| XSMAD1 full-length | ND |
| XSMAD1 N-domain | − |

-continued

| | |
|---|---|
| mSMAD1 C-domain | +++ |
| mSMAD2 C-domain | ND |
| mSMAD5 C-domain | +++ |
| XSMAD1 C-domain del 424–466 | − |
| XSMAD1 C-domain G418S | + |

SIP5 (also called clone th76).
Analysis of interaction of the SIP5 prey protein with different bait proteins (which are described in the data section obtained with SIP 1) in a yeast two-hybrid assay can be summarized as follows

| | |
|---|---|
| Empty bait vector pGBT9 | − |
| Full-length XSMAD1 | + |
| XSMAD1 C-domain | + |
| XSMAD1 C-domain G418S | + |
| Mouse SMAD2 C-domain | + |
| Mouse SMAD5 C-domain | + |
| Lamin (pLAM; Clontech) | − |

SIP7 (also called clone th74)
Analysis of the interaction of the SIP7 prey protein with different bait proteins in a yeast two-hybrid assay can be summarized as follows:

| | |
|---|---|
| PGBT9 | − |
| Full-length XSMAD1 | − |
| XSMAD1 C-domain | + |
| XSMAD1 C-domain, G418S | + |
| XSMAD1 C-domain del aa 424–466 | − |
| XSMAD1 N-terminal domain | − |
| Mouse SMAD2 C-domain | + |
| Mouse SMAD5 C-domain | + |
| Lamin (pLAM) | − |

The following clones have been investigated less extensively. They are considered as "true positives" because they interact with the XSMAD1 C-domain bait and not with the empty bait (i.e., GAL-4 DBD alone)
TH75
Three independent clones isolated (th75, th83, th89)
Partial aa sequences do not show significant homology to proteins in the public databases
Interactions in yeast:

| | |
|---|---|
| XSMAD1 C-domain bait | +++ |
| Empty bait | − |

TH92
Zinc finger protein
homology to KUP
T1179, T186, TH90
Partial sequences do not display significant homology to any protein sequence in the public databases.

Clones available in the sequence listing as conversion table from clone notation to sequence listing notation

| | |
|---|---|
| SIP 1 nucleotide sequence = | SEQ ID NO: 1 |
| SIP 1 amino acid sequence = | SEQ ID NO: 2 |
| SIP 2 nucleotide sequence = | SEQ ID NO: 3 |
| SIP 2 amino acid sequence = | SEQ ID NO: 4 |
| TH60(TH77) = | SEQ ID NO: 5 |
| TH72(DPC4 or SMAD4) = | SEQ ID NO: 6 |
| TH72\R = | SEQ ID NO: 7 |
| SIP 7(th74) = | SEQ ID NO: 8 |
| TH75F(TH83F, TH89F) = | SEQ ID NO: 9 |
| SIP 5(th76) = | SEQ ID NO: 10 |
| TH79F = | SEQ ID NO: 11 |
| TH79R = | SEQ ID NO: 12 |
| TH83R = | SEQ ID NO: 13 |
| TH86F = | SEQ ID NO: 14 |
| TH86R = | SEQ ID NO: 15 |
| TH89 = TH75R = | SEQ ID NO: 16 |
| TH90F = | SEQ ID NO: 17 |
| TH90R = | SEQ ID NO: 18 |
| TH92F = | SEQ ID NO: 19 |
| TH92R = | SEQ ID NO: 20 |

What is claimed is:

1. An isolated SMAD interacting protein or fragment thereof produced by the process comprising:
   conducting a two-hybrid screening assay, wherein a SMAD C-terminal domain from SMAD1, SMAD2, or SMAD5 fused to a DNA binding domain is used as bait and a vertebrate cDNA library is used as prey in said tow hybrid screening assay;
   identifying a SMAD interacting protein or fragment thereof in said two-hybrid assay;
   determining that the SMAD interacting protein or fragment thereof binds to E2 box sites and interferes with Brachyury-mediated transcription activation in cells; and
   isolating said SMAD interacting protein or fragment thereof.

2. SMAD interacting protein of the family of zinc finger/homeodomain proteins including d-crystallin enhancer binding protein and Drosophila zfh-1, wherein said SMAD interacting protein:
   does not interact with full size XSMAD1 in yeast,
   binds to E2 box sites,
   binds to the Brachyury protein binding site,
   interferes with Brachyury-mediated transcription activation in cells, and
   interacts with a C-domain of SMAD 1, 2 and 5.

3. An isolated polypeptide comprising the amino acid sequence of SEQ ID NO: 2 or a functional fragment thereof, wherein said functional fragment binds to the SMAD 1 C-domain in a yeast two-hybrid assay, wherein said SMAD1 C-domain is expressed as a DNA-binding domain fusion in said assay.

4. A pharmaceutical composition comprising the polypeptide of claim 3, together with a suitable carrier.

5. The isolated polypeptide of claim 3, wherein the functional fragment is selected from the group consisting of amino acids 44–236 of SEQ ID NO:2, amino acids 166–236 of SEQ ID NO:2, and amino acids 44–216 of SEQ ID NO:2.

6. An isolated polypeptide comprising the amino acid sequence depicted as the one letter code QHLGVGMEAPLLGFPTMNSNLSEVQKVL QIVDNTVSRQKMDCKTEDISKLK (SEQ ID NO: 21) necessary for binding with SMAD.

7. An isolated polypeptide comprising the amino acid sequence of SEQ ID NO: 2 or a fragment that binds to an E2 box site in an electrophoretic mobility shift assay.

8. The isolated polypeptide of claim 7, wherein the functional fragment comprises amino acids 77–214 of SEQ ID NO: 2.

* * * * *

UNITED STATES PATENT AND TRADEMARK OFFICE
CERTIFICATE OF CORRECTION

PATENT NO. : 6,884,779 B2
APPLICATION NO. : 09/964238
DATED : April 26, 2005
INVENTOR(S) : Kristin Verschueren, Jacques Remacle and Danny Huylebroek It is certified that error appears in the above-identified patent and that said Letters Patent is hereby corrected as shown below:

On the title page:
In ITEM (57) ABSTRACT, 1st line, change "protein" to --protein(s)--
In ITEM (57) ABSTRACT, 2nd line, delete "(s)" at the beginning of the line
In ITEM (57) ABSTRACT, 10th line, change "Brachyury" to --*Brachyury*--
In ITEM (57) ABSTRACT, 11th line, change "Brachyury-mediated" to --*Brachyury*-mediated--

| | | |
|---|---|---|
| COLUMN 2, | LINE 65, | change "TGF-B" to --TGF-$\beta$-- |
| COLUMN 7, | LINE 32, | change "(GAL4" to --(GAL4$_{DBD}$)-- |
| COLUMN 7, | LINE 33, | delete "DBD)" |
| COLUMN 10, | LINE 65, | change "TGF-B" to --TGF-$\beta$-- |
| COLUMN 11, | LINE 20, | change "TGF-$\delta$-" to --TGF-$\beta$- -- |
| COLUMN 11, | LINE 40, | change "BMP4)." to --BMP-4).-- |
| COLUMN 12, | LINE 57, | change "th 12." to --th12.-- |
| COLUMN 14, | LINE 29, | change "are-described" to --are described-- |
| COLUMN 15, | LINES 31-38, | delete the duplicate paragraph beginning "SIP7 partial" and ending with "in SEQ ID NO: 8." in its entirety. |
| COLUMN 15, | LINE 48, | change "long, and" to --long and-- |
| COLUMN 16, | LINE 2, | change "(TH 1)" to --(TH1)-- |
| COLUMN 16, | LINE 9, | change "PolyA$^{30}$" to --PolyA$^{+}$-- |
| COLUMN 16, | LINE 24, | change "operation of" to --preparation of-- |
| COLUMN 18, | LINE 62, | change "T1179, T186, TH90" to --TH79, TH86, TH90-- |

UNITED STATES PATENT AND TRADEMARK OFFICE
CERTIFICATE OF CORRECTION

PATENT NO.        : 6,884,779 B2
APPLICATION NO.   : 09/964238
DATED             : April 26, 2005
INVENTOR(S)       : Kristin Verschueren, Jacques Remacle and Danny Huylebroek It is certified that error appears in the above-identified patent and that said Letters Patent is hereby corrected as shown below:

CLAIM 1, COLUMN 49, LINE 56,   change "DNA binding" to --DNA-binding--
CLAIM 1, COLUMN 49, LINE 58,   change "tow hybrid" to --two-hybrid--

Signed and Sealed this

Thirtieth Day of September, 2008

JON W. DUDAS
*Director of the United States Patent and Trademark Office*

SEQUENCE LISTING

```
<160> NUMBER OF SEQ ID NOS: 27

<210> SEQ ID NO 1
<211> LENGTH: 3006
<212> TYPE: DNA
<213> ORGANISM: Mus musculus

<400> SEQUENCE: 1
gcagcactca gcaccaaatg ctaacccaag gagcaggtaa ccgcaagttc aagtgcacgg      60
agtgtggcaa ggccttcaag tacaagcacc acctgaaaga cacctgaga attcacagtg     120 gtgaaaaacc ttacgaatgc ccaaactgca agaaacgctt ctctcattct gggtcctaca     180
gttcacatat cagcagcaag aaatgtattg gtttaatatc agtaaatggc cgaatgagaa     240
acaatatcaa gacgggttct tcccctaatt ctgtttcttc ttctcctact aactcagcca     300
ttactcagtt aaggaacaag ttggaaaatg gaaaaccact tagcatgtct gagcagacag     360
gcttacttaa gattaaaaca gaaccactag acttcaatga ctataaagtt cttatggcaa     420
cacatggggt tagtggcagc agtcccttta tgaacggtgg gcttggagcc accagccctt     480
taggtgtaca cccatctgct cagagtccaa tgcagcactt aggtgtaggg atggaagccc     540
ctttacttgg atttccccact atgaatagta acttgagtga ggtacaaaag gttctacaga     600
ttgtggacaa tacggtttct aggcaaaaga tggactgcaa gacggaagac atttcaaagt     660
tgaaaggtta tcacatgaag gatccatgtt ctcagccaga agaacaaggg gtaacttctc     720
ccaatattcc ccctgtcggt cttccagtag tgagtcataa cggtgccact aaaagtatta     780
ttgactatac cttagagaaa gtcaatgaag ccaaagcttg cctccagagc ttgaccaccg     840
actcaaggag acagatcagt aacataaaga agagaagtt gcgtactttg atagatttgg     900
tcactgatga taaaatgatt gagaaccaca gcatatccac tccattttca tgccagttct     960
gtaaagaaag cttcccgggc cctattcccc tgcatcagca tgaacgatac ctgtgtaaga    1020
tgaatgaaga gatcaaggca gtcctgcaac ctcatgaaaa catagtcccc aacaaagctg    1080 gagttttgt tgataataaa gccctcctct tgtcatctgt actttccgag aaaggactga    1140
caagccccat caacccatac aaggaccaca tgtctgtact gaaagcatac tatgctatga    1200
acatggagcc caactctgat gaactgctga aaatctccat tgctgtgggc cttcctcagg    1260
aatttgtgaa ggaatggttt gagcaaagaa aagtctacca gtattcgaat tccaggtcac    1320
catcactgga aaggacctcc aagccgttag ctcccaacag taacccacc acaaaaagact    1380
```

-continued

```
ctttgttacc caggtctcct gtaaaaccta tggactccat cacatcgcca tctatagcag   1440
aactccacaa cagtgttacg agttgtgatc ctcctctcag gctaacaaaa tcttcccatt   1500
tcaccaatat aaagcagtt gataaactgg accactcgag gagtaatact ccttctcctt    1560
taaatctttc ctccacatct tctaaaaact cccacagtag ctcgtacact ccaaatagct   1620
tctcttccga ggagctgcag gctgagccgt tggacctgtc attaccaaaa caaatgagag   1680
aacccaaagg tattatagcc acaagaaca aaacaaaagc tactagcata aacttagacc    1740
acaacagtgt ttcttcatcg tctgagaatt cagatgagcc tctgaatttg acttttatca   1800
agaaagagtt ttcaaattct aataacctgg acaataaaag caacaaccct gtgttcggca   1860
tgaacccatt tagtgccaag cctttataca ccctcttcc accacagagc gcatttcccc    1920
ctgccacttt catgccacca gtccagacca gcatccccgg gctacgacca tacccaggac   1980
tggatcagat gagcttccta ccgcatatgg cctatacta cccaacggga gcagctacct    2040
ttgctgatat gcagcaaagg aggaaatacc agaggaaaca aggatttcag ggagacttgc   2100
tggatggagc acaagactac atgtcaggcc tagatgacat gacagactcc gattcctgtc   2160
tgtctcgaaa aagataaag aagacagaaa gtggcatgta tgcatgtgac ttatgtgaca    2220
agacattcca gaaaagcagt tcccttctgc gacataaata cgaacacaca ggaaagagac   2280
cacaccagtg tcagatttgt aagaaagcgt tcaaacacaa acaccacctt atcgagcact   2340
cgaggctgca ctcgggcgag aagccctatc agtgtgacaa atgtggcaag cgcttctcac   2400
actcgggctc ctactcgcag cacatgaatc acaggtactc ctactgcaag cgggaggcgg   2460
aggagcggga agcagccgag cgcgaggcgc gagagaaagg gcacttggga cccaccgagc   2520
tgctgatgaa ccgggcttac ctgcagagca tcacccctca ggggtactct gactcggagg   2580
agagggagag catgccgagg gatggcgaga gcgagaagga gcacgagaag gagggcgagg   2640
agggttatgg gaagctgcgg agaagggacg gcgacgagga ggaagaggag gaagaggaag   2700
aaagtgaaaa taaaagtatg gatacggatc ccgaaacgat acgggatgag gaagagactg   2760
gggatcactc gatggacgac agttcagagg atgggaaaat ggaaaccaaa tcagaccacg   2820
aggaagacaa tatggaagat ggcatgggat aaactactgc attttaagct tcctattttt   2880
tttttccagt agtattgtta cctgcttgaa aacactgctg tgttaagctg ttcatgcacg   2940
tgcctgacgc ttccaggaag ctgtagagag ggacaaaaag gggcacttca gccaagtctg   3000
agttag                                                              3006
```

<210> SEQ ID NO 2
<211> LENGTH: 944
<212> TYPE: PRT
<213> ORGANISM: Mus musculus

<400> SEQUENCE: 2

```
Met Leu Thr Gln Gly Ala Gly Asn Arg Lys Phe Lys Cys Thr Glu Cys
1               5                   10                  15

Gly Lys Ala Phe Lys Tyr Lys His His Leu Lys Glu His Leu Arg Ile
            20                  25                  30

His Ser Gly Glu Lys Pro Tyr Glu Cys Pro Asn Cys Lys Lys Arg Phe
        35                  40                  45

Ser His Ser Gly Ser Tyr Ser Ser His Ile Ser Ser Lys Lys Cys Ile
    50                  55                  60

Gly Leu Ile Ser Val Asn Gly Arg Met Arg Asn Asn Ile Lys Thr Gly
65                  70                  75                  80
```

```
Ser Ser Pro Asn Ser Val Ser Ser Pro Thr Asn Ser Ala Ile Thr
            85                  90              95

Gln Leu Arg Asn Lys Leu Glu Asn Gly Lys Pro Leu Ser Met Ser Glu
            100                 105             110

Gln Thr Gly Leu Leu Lys Ile Lys Thr Glu Pro Leu Asp Phe Asn Asp
            115                 120             125

Tyr Lys Val Leu Met Ala Thr His Gly Phe Ser Gly Ser Ser Pro Phe
            130                 135             140

Met Asn Gly Gly Leu Gly Ala Thr Ser Pro Leu Gly Val His Pro Ser
145                 150                 155             160

Ala Gln Ser Pro Met Gln His Leu Gly Val Gly Met Glu Ala Pro Leu
                165                 170             175

Leu Gly Phe Pro Thr Met Asn Ser Asn Leu Ser Glu Val Gln Lys Val
            180                 185             190

Leu Gln Ile Val Asp Asn Thr Val Ser Arg Gln Lys Met Asp Cys Lys
            195                 200             205

Thr Glu Asp Ile Ser Lys Leu Lys Gly Tyr His Met Lys Asp Pro Cys
210                 215                 220

Ser Gln Pro Glu Glu Gln Gly Val Thr Ser Pro Asn Ile Pro Pro Val
225                 230                 235             240

Gly Leu Pro Val Val Ser His Asn Gly Ala Thr Lys Ser Ile Ile Asp
            245                 250             255

Tyr Thr Leu Glu Lys Val Asn Glu Ala Lys Ala Cys Leu Gln Ser Leu
            260                 265             270

Thr Thr Asp Ser Arg Arg Gln Ile Ser Asn Ile Lys Lys Glu Lys Leu
            275                 280             285

Arg Thr Leu Ile Asp Leu Val Thr Asp Lys Met Ile Glu Asn His
            290                 295             300

Ser Ile Ser Thr Pro Phe Ser Cys Gln Phe Cys Lys Glu Ser Phe Pro
305                 310                 315             320

Gly Pro Ile Pro Leu His Gln His Glu Arg Tyr Leu Cys Lys Met Asn
            325                 330             335

Glu Glu Ile Lys Ala Val Leu Gln Pro His Glu Asn Ile Val Pro Asn
            340                 345             350

Lys Ala Gly Val Phe Val Asp Asn Lys Ala Leu Leu Leu Ser Ser Val
            355                 360             365

Leu Ser Glu Lys Gly Leu Thr Ser Pro Ile Asn Pro Tyr Lys Asp His
    370                 375             380

Met Ser Val Leu Lys Ala Tyr Tyr Ala Met Asn Met Glu Pro Asn Ser
385                 390                 395             400

Asp Glu Leu Leu Lys Ile Ser Ile Ala Val Gly Leu Pro Gln Glu Phe
            405                 410             415

Val Lys Glu Trp Phe Glu Gln Arg Lys Val Tyr Gln Tyr Ser Asn Ser
            420                 425             430

Arg Ser Pro Ser Leu Glu Arg Thr Ser Lys Pro Leu Ala Pro Asn Ser
            435                 440             445

Asn Pro Thr Thr Lys Asp Ser Leu Leu Pro Arg Ser Pro Val Lys Pro
            450                 455             460

Met Asp Ser Ile Thr Ser Pro Ser Ile Ala Glu Leu His Asn Ser Val
465                 470                 475             480

Thr Ser Cys Asp Pro Pro Leu Arg Leu Thr Lys Ser Ser His Phe Thr
            485                 490             495

Asn Ile Lys Ala Val Asp Lys Leu Asp His Ser Arg Ser Asn Thr Pro
```

```
                  500                 505                 510
Ser Pro Leu Asn Leu Ser Ser Thr Ser Ser Lys Asn Ser His Ser Ser
            515                 520                 525
Ser Tyr Thr Pro Asn Ser Phe Ser Ser Glu Glu Leu Gln Ala Glu Pro
            530                 535                 540
Leu Asp Leu Ser Leu Pro Lys Gln Met Arg Glu Pro Lys Gly Ile Ile
545                 550                 555                 560
Ala Thr Lys Asn Lys Thr Lys Ala Thr Ser Ile Asn Leu Asp His Asn
            565                 570                 575
Ser Val Ser Ser Ser Glu Asn Ser Asp Glu Pro Leu Asn Leu Thr
            580                 585                 590
Phe Ile Lys Lys Glu Phe Ser Asn Ser Asn Asn Leu Asp Asn Lys Ser
            595                 600                 605
Asn Asn Pro Val Phe Gly Met Asn Pro Phe Ser Ala Lys Pro Leu Tyr
            610                 615                 620
Thr Pro Leu Pro Pro Gln Ser Ala Phe Pro Ala Thr Phe Met Pro
625                 630                 635                 640
Pro Val Gln Thr Ser Ile Pro Gly Leu Arg Pro Tyr Pro Gly Leu Asp
            645                 650                 655
Gln Met Ser Phe Leu Pro His Met Ala Tyr Thr Tyr Pro Thr Gly Ala
            660                 665                 670
Ala Thr Phe Ala Asp Met Gln Gln Arg Arg Lys Tyr Gln Arg Lys Gln
            675                 680                 685
Gly Phe Gln Gly Asp Leu Leu Asp Gly Ala Gln Asp Tyr Met Ser Gly
            690                 695                 700
Leu Asp Asp Met Thr Asp Ser Asp Ser Cys Leu Ser Arg Lys Lys Ile
705                 710                 715                 720
Lys Lys Thr Glu Ser Gly Met Tyr Ala Cys Asp Leu Cys Asp Lys Thr
            725                 730                 735
Phe Gln Lys Ser Ser Ser Leu Leu Arg His Lys Tyr Glu His Thr Gly
            740                 745                 750
Lys Arg Pro His Gln Cys Gln Ile Cys Lys Lys Ala Phe Lys His Lys
            755                 760                 765
His His Leu Ile Glu His Ser Arg Leu His Ser Gly Glu Lys Pro Tyr
            770                 775                 780
Gln Cys Asp Lys Cys Gly Lys Arg Phe Ser His Ser Gly Ser Tyr Ser
785                 790                 795                 800
Gln His Met Asn His Arg Tyr Ser Tyr Cys Lys Arg Glu Ala Glu Glu
            805                 810                 815
Arg Glu Ala Ala Glu Arg Glu Ala Arg Glu Lys Gly His Leu Gly Pro
            820                 825                 830
Thr Glu Leu Leu Met Asn Arg Ala Tyr Leu Gln Ser Ile Thr Pro Gln
            835                 840                 845
Gly Tyr Ser Asp Ser Glu Glu Arg Glu Ser Met Pro Arg Asp Gly Glu
            850                 855                 860
Ser Glu Lys Glu His Glu Lys Glu Gly Glu Gly Tyr Gly Lys Leu
865                 870                 875                 880
Arg Arg Arg Asp Gly Asp Glu Glu Glu Glu Glu Glu Glu Glu Ser
            885                 890                 895
Glu Asn Lys Ser Met Asp Thr Asp Pro Glu Thr Ile Arg Asp Glu Glu
            900                 905                 910
Glu Thr Gly Asp His Ser Met Asp Asp Ser Ser Glu Asp Gly Lys Met
            915                 920                 925
```

-continued

Glu Thr Lys Ser Asp His Glu Glu Asp Asn Met Glu Asp Gly Met Gly
   930               935                  940

<210> SEQ ID NO 3
<211> LENGTH: 2959
<212> TYPE: DNA
<213> ORGANISM: Mus musculus

<400> SEQUENCE: 3

| | | | | | |
|---|---|---|---|---|---|
| ctggctaggc | gtcgcggact | ccggagatgg | aggaaaagga | gcagctgcgg | cggcagatac | 60 |
| gcctcctgca | gggtctaatt | gatgactata | aacactcca | cggcaatggc | cctgccctgg | 120 |
| gcaactcatc | agctactcgg | tggcagccac | ccgtgttccc | gggtggcagg | acctttggcg | 180 |
| cccgctactc | ccgtccaagt | cggagggct | tctcctcaca | ccatggccct | tcgtggcgca | 240 |
| agaaatactc | ccttgtgaat | cagcctgtgg | aatcttctga | cccagccagc | gatcctgctt | 300 |
| ttcagacatc | cctcaggtct | gaggatagcc | agcatcctga | ccccagcag | tatgtactgg | 360 |
| agagacaggt | ccagctcagt | ccagatcaga | atatggttat | taagatcaag | ccaccatcaa | 420 |
| agtcaggtgc | catcaatgct | tcaggggtcc | agcgggggtc | cttggaaggc | tgtgatgacc | 480 |
| cctcttggag | tggccaaaga | ccccaaggaa | gtgaggttga | ggtccctggt | ggacaactgc | 540 |
| agcctgcaag | gccaggaaga | accaaggtgg | gttacagtgt | ggacgacccc | ctcttggtct | 600 |
| gccagaagga | gcctggcaag | cctcgggtag | tgaagtctgt | gggcagggtg | agtgacagct | 660 |
| ctcccgagca | tcggcggaca | gtcagtgaaa | atgaagtggc | cctcagggta | cacttcccat | 720 |
| ctgtcctgcc | ccatcacact | gctgtggctc | tgggcaggaa | ggtaggccct | cattctacca | 780 |
| gctattctga | acagttcatt | ggagaccaaa | gagcaaacac | tggccactca | gaccagccag | 840 |
| cttccttggg | gccagtggtg | gcttcagtca | gaccagcaac | agccaggcag | gtcagggagg | 900 |
| cctcactgct | cgtgtcctgt | cgaaccagca | agtttcggaa | aaacaactac | aaatgggtag | 960 |
| ctgcctcaga | aaagagccca | cgggtcgctc | ggagagccct | cagtcccaga | caaactctgg | 1020 |
| agagcgggaa | caaggccact | ttgggtacag | ttggaaagac | agagaagcca | cagcctaaag | 1080 |
| ttgacccaga | ggtgaggccg | gagaaactgg | ccacaccatc | caagcctggc | ctctctccca | 1140 |
| gcaagtacaa | gtggaaggct | tccagcccgt | ctgcttcctc | ctcttcctct | ttccgttggc | 1200 |
| agtctgaggc | tggcagcaag | gaccatactt | ctcagctctc | cccagtccca | tctaggccca | 1260 |
| catcagggga | cagaccagca | gggggaccca | gcagcttgaa | gcccctcttt | ggagagtcac | 1320 |
| agctctcagc | ttacaaagtg | aagagccgga | ccaagattat | ccggaggcgg | ggcaatacca | 1380 |
| gcattcctgg | ggacaagaag | aacagcccta | caactgccac | caccagcaaa | aaccatctta | 1440 |
| cccagcgacg | gagacaggcc | ctccggggga | agaatagccc | ggttctaagg | aagactcccc | 1500 |
| acaagggtct | gatgcaggtc | aacaggcacc | ggctctgctg | cctgccgtcc | agccggaccc | 1560 |
| acctctccac | caaggaagct | tccagtgtgc | acatggggat | tccaccctcc | aataaggtga | 1620 |
| tcaagacccg | ctaccgcatt | gttaagaaga | ccccaagctc | ttcctttggt | gctccatcct | 1680 |
| tcccctcatc | tctaccctcc | tggcgggccc | ggcgcatccc | attatccagg | tccctagtgc | 1740 |
| taaaccgcct | tcgtccagca | atcactgggg | gagggaaagc | cccacctggt | accctcgat | 1800 |
| ggcgcaacaa | aggctaccgc | tgcattgag | gggttctgta | caaggtgtct | gccaacaagc | 1860 |
| tctccaaaac | ttctagcagg | cccagtgatg | gcaacaggac | cctcctccgc | acaggacgcc | 1920 |
| tggaccctgc | taccacctgc | agtcgttcct | tggccagccg | ggccatccag | cggagcctgg | 1980 |
| ctatcatccg | gcaggcgaag | cagaagaaag | agaagaagag | agagtactgc | atgtactaca | 2040 |

```
accgctttgg caggtgtaac cgtggcgaat gctgcccta catccatgac cctgagaagg    2100
tggccgtgtg caccagattt gtccgaggca catgcaagaa gacagatggg tcctgccctt    2160
tctctcacca tgtgtccaag gaaaagatgc ctgtgtgctc ctactttctg aagggatct     2220 gcagcaacag caactgcccc tacagccatg tgtacgtgtc ccgcaaggct gaagtctgca    2280
gtgacttcct caaaggctac tgcccattgg gtgcaaagtg caagaagaag cacacgctgc    2340
tgtgtcctga cttttgcccgc aggggtattt gtccccgtgg ctcccagtgc cagctgctcc   2400
atcgtaacca gaagcgacat ggccggcgga cagctgcacc tcctatccct gggcccagtg    2460
atggagcccc cagaagcaag gcctcagctg ccacgtact caggaagcct actactactc     2520
agcgctctgt cagacagatg tccagtggtc tggcttccgg agctgaggcc ccagcctccc    2580
cacctccctc cccaagggta ttagcctcca cctctaccct gtcttcaaag gccaccgctg    2640
cctcctctcc ttcccctct ccctctacta gctccccagc cccttccttg gagcaggaag     2700
aagctgtctc tgggacaggc tcaggaacag gctccagtgg cctctgcaag ctgccatcct    2760
tcatctccct gcactcctcc ccaagccag gaggacagac tgagactggg ccccaggccc     2820
ccaggagccc tcgcaccaag gactcaggga agccgctaca catcaaacca cgcctgtgag    2880 gcccctgag gaccagcccg cacctacctc agaccctcac ccctggagag gatgaaggct     2940
ctacccacaa ctgctcctg                                                 2959

<210> SEQ ID NO 4
<211> LENGTH: 950
<212> TYPE: PRT
<213> ORGANISM: Mus musculus

<400> SEQUENCE: 4

Met Glu Glu Lys Glu Gln Leu Arg Arg Gln Ile Arg Leu Leu Gln Gly
1               5                   10                  15

Leu Ile Asp Asp Tyr Lys Thr Leu His Gly Asn Gly Pro Ala Leu Gly
            20                  25                  30

Asn Ser Ser Ala Thr Arg Trp Gln Pro Pro Val Phe Pro Gly Gly Arg
        35                  40                  45

Thr Phe Gly Ala Arg Tyr Ser Arg Pro Ser Arg Arg Gly Phe Ser Ser
    50                  55                  60

His His Gly Pro Ser Trp Arg Lys Lys Tyr Ser Leu Val Asn Gln Pro
65                  70                  75                  80

Val Glu Ser Ser Asp Pro Ala Ser Asp Pro Ala Phe Gln Thr Ser Leu
                85                  90                  95

Arg Ser Glu Asp Ser Gln His Pro Glu Pro Gln Gln Tyr Val Leu Glu
            100                 105                 110

Arg Gln Val Gln Leu Ser Pro Asp Gln Asn Met Val Ile Lys Ile Lys
        115                 120                 125

Pro Pro Ser Lys Ser Gly Ala Ile Asn Ala Ser Gly Val Gln Arg Gly
    130                 135                 140

Ser Leu Glu Gly Cys Asp Asp Pro Ser Trp Ser Gly Gln Arg Pro Gln
145                 150                 155                 160

Gly Ser Glu Val Glu Val Pro Gly Gly Gln Leu Gln Pro Ala Arg Pro
                165                 170                 175

Gly Arg Thr Lys Val Gly Tyr Ser Val Asp Asp Pro Leu Leu Val Cys
            180                 185                 190

Gln Lys Glu Pro Gly Lys Pro Arg Val Val Lys Ser Val Gly Arg Val
        195                 200                 205
```

-continued

```
Ser Asp Ser Ser Pro Glu His Arg Arg Thr Val Ser Glu Asn Glu Val
    210                 215                 220
Ala Leu Arg Val His Phe Pro Ser Val Leu Pro His Thr Ala Val
225                 230                 235                 240
Ala Leu Gly Arg Lys Val Gly Pro His Ser Thr Ser Tyr Ser Glu Gln
                245                 250                 255
Phe Ile Gly Asp Gln Arg Ala Asn Thr Gly His Ser Asp Gln Pro Ala
            260                 265                 270
Ser Leu Gly Pro Val Val Ala Ser Val Arg Pro Ala Thr Ala Arg Gln
        275                 280                 285
Val Arg Glu Ala Ser Leu Leu Val Ser Cys Arg Thr Ser Lys Phe Arg
    290                 295                 300
Lys Asn Asn Tyr Lys Trp Val Ala Ala Ser Glu Lys Ser Pro Arg Val
305                 310                 315                 320
Ala Arg Arg Ala Leu Ser Pro Arg Thr Thr Leu Glu Ser Gly Asn Lys
                325                 330                 335
Ala Thr Leu Gly Thr Val Gly Lys Thr Glu Lys Pro Gln Pro Lys Val
            340                 345                 350
Asp Pro Glu Val Arg Pro Glu Lys Leu Ala Thr Pro Ser Lys Pro Gly
        355                 360                 365
Leu Ser Pro Ser Lys Tyr Lys Trp Lys Ala Ser Pro Ser Ala Ser
    370                 375                 380
Ser Ser Ser Ser Phe Arg Trp Gln Ser Glu Ala Gly Ser Lys Asp His
385                 390                 395                 400
Thr Ser Gln Leu Ser Pro Val Pro Ser Arg Pro Thr Ser Gly Asp Arg
                405                 410                 415
Pro Ala Gly Gly Pro Ser Ser Leu Lys Pro Leu Phe Gly Glu Ser Gln
            420                 425                 430
Leu Ser Ala Tyr Lys Val Lys Ser Arg Thr Lys Ile Ile Arg Arg Arg
        435                 440                 445
Gly Asn Thr Ser Ile Pro Gly Asp Lys Lys Asn Ser Pro Thr Thr Ala
    450                 455                 460
Thr Thr Ser Lys Asn His Leu Thr Gln Arg Arg Gln Ala Leu Arg
465                 470                 475                 480
Gly Lys Asn Ser Pro Val Leu Arg Lys Thr Pro His Lys Gly Leu Met
                485                 490                 495
Gln Val Asn Arg His Arg Leu Cys Cys Leu Pro Ser Ser Arg Thr His
            500                 505                 510
Leu Ser Thr Lys Glu Ala Ser Ser Val His Met Gly Ile Pro Pro Ser
        515                 520                 525
Asn Lys Val Ile Lys Thr Arg Tyr Arg Ile Val Lys Lys Thr Pro Ser
    530                 535                 540
Ser Ser Phe Gly Ala Pro Ser Phe Pro Ser Ser Leu Pro Ser Trp Arg
545                 550                 555                 560
Ala Arg Arg Ile Pro Leu Ser Arg Ser Leu Val Leu Asn Arg Leu Arg
                565                 570                 575
Pro Ala Ile Thr Gly Gly Lys Ala Pro Pro Gly Thr Pro Arg Trp
            580                 585                 590
Arg Asn Lys Gly Tyr Arg Cys Ile Gly Gly Val Leu Tyr Lys Val Ser
        595                 600                 605
Ala Asn Lys Leu Ser Lys Thr Ser Ser Arg Pro Ser Asp Gly Asn Arg
    610                 615                 620
```

-continued

```
Thr Leu Leu Arg Thr Gly Arg Leu Asp Pro Ala Thr Thr Cys Ser Arg
625                 630                 635                 640

Ser Leu Ala Ser Arg Ala Ile Gln Arg Ser Leu Ala Ile Ile Arg Gln
            645                 650                 655

Ala Lys Gln Lys Glu Lys Lys Arg Glu Tyr Cys Met Tyr Tyr Asn
        660                 665                 670

Arg Phe Gly Arg Cys Asn Arg Gly Glu Cys Cys Pro Tyr Ile His Asp
        675                 680                 685

Pro Glu Lys Val Ala Val Cys Thr Arg Phe Val Arg Gly Thr Cys Lys
    690                 695                 700

Lys Thr Asp Gly Ser Cys Pro Phe Ser His His Val Ser Lys Glu Lys
705                 710                 715                 720

Met Pro Val Cys Ser Tyr Phe Leu Lys Gly Ile Cys Ser Asn Ser Asn
                725                 730                 735

Cys Pro Tyr Ser His Val Tyr Val Ser Arg Lys Ala Glu Val Cys Ser
            740                 745                 750

Asp Phe Leu Lys Gly Tyr Cys Pro Leu Gly Ala Lys Cys Lys Lys Lys
        755                 760                 765

His Thr Leu Leu Cys Pro Asp Phe Ala Arg Arg Gly Ile Cys Pro Arg
    770                 775                 780

Gly Ser Gln Cys Gln Leu Leu His Arg Asn Gln Lys Arg His Gly Arg
785                 790                 795                 800

Arg Thr Ala Ala Pro Pro Ile Pro Gly Pro Ser Asp Gly Ala Pro Arg
                805                 810                 815

Ser Lys Ala Ser Ala Gly His Val Leu Arg Lys Pro Thr Thr Thr Gln
            820                 825                 830

Arg Ser Val Arg Gln Met Ser Ser Gly Leu Ala Ser Gly Ala Glu Ala
        835                 840                 845

Pro Ala Ser Pro Pro Ser Pro Arg Val Leu Ala Ser Thr Ser Thr
    850                 855                 860

Leu Ser Ser Lys Ala Thr Ala Ala Ser Ser Pro Ser Pro Ser Pro Ser
865                 870                 875                 880

Thr Ser Ser Pro Ala Pro Ser Leu Glu Gln Glu Glu Ala Val Ser Gly
                885                 890                 895

Thr Gly Ser Gly Thr Gly Ser Ser Gly Leu Cys Lys Leu Pro Ser Phe
            900                 905                 910

Ile Ser Leu His Ser Ser Pro Ser Pro Gly Gly Gln Thr Glu Thr Gly
        915                 920                 925

Pro Gln Ala Pro Arg Ser Pro Arg Thr Lys Asp Ser Gly Lys Pro Leu
    930                 935                 940

His Ile Lys Pro Arg Leu
945                 950
```

<210> SEQ ID NO 5
<211> LENGTH: 1409
<212> TYPE: DNA
<213> ORGANISM: Mus musculus
<220> FEATURE:
<221> NAME/KEY: misc_feature
<222> LOCATION: (873)..(873)
<223> OTHER INFORMATION: n can be any nucleotide

<400> SEQUENCE: 5
gaggcttcga aagtgctgaa agcagatggg aaggctgcgc tgcccccaag agggctgtgg      60
ggctgccttc tccagcctca tgggttatca ataccaccag cggcgctgtg ggaagccacc    120

```
ctgtgaggta gacagtccct ccttcccctg tacccactgt ggcaagactt accgatccaa      180
ggctggccac gactatcatg tgcgttcaga gcacacagcc ccgcctcctg aggatcccac      240
agacaagatc cctgaggctg aggacctgct tggggtagaa cggacccccaa gtggtcgcat     300 ccgacgtacg tgcccaggtt gccgtgttcc atctacagga gattgcagag atgaactggc      360
ccgtgactgg accaaacaac gcatgaagga tgacttgtgc ctgagaatgc acgactcaac      420
tacactcggc caggtctccc cacacttaac cctcagctgc tggaagcatg gaagaatgaa      480
gtcaaggaga agggccatgt gaactgtccc aatgaattgc tgtgaagcca tctacgccag      540
tgtgtccggc tcaaggccc atcttgccag ctgcagcaag ggggaccacc tgggtgggga      600
aagtaccgct gcctgctgtg tcccaaagaa gttcagctct gaaaagcggc gtgaagttac      660
cacatcctta aagacccaac gggagagaat tggttccgga cctcagctga cccgtcttcc      720
aacacaagag ccaggactcc ttgatgccta ggaaagagaa agaaatttgt cagggagaaa      780 gaagcgggc cgcaaaccca aggaacgatc ctccgaggag ccagcatctg ctcccccta       840 acagggaatg actggccccc aggaggcaga ganagggggt cccggagctc cactgggaag      900
aaggctggag ctgggaaggc acctgaaaag tgagcctagt gggcagggcc tacccatcat      960
gccctgcatt gtccagatta ggggagccag ttctagactg gtcctccacc tccaacacac     1020 accccccatct gtccagaggg ttggcaaact actctgctct ccctgaaagt ggtccttccc    1080
ctgtttaggc tgcctcaaca aggctagatg gggctccccg ggagtgccag gcagcagca     1140 aaagtgcaat aggctggagg acccagccgt tcctacaagg acattgcatg gcaggagcct     1200
tggcatcatg gggcatgaag tgtgcttaaa cagttaaaag gtcccagttt ccaccttcct     1260
ctggcccagt aggatcccca atctgactct ttcaaggctc agacattcct ggtgacccaa     1320
tgttgtggac tgatgaggca cctgagcagt ctggctgcca taacttgggc ctcgcctcca     1380
cccaacactg gaactccagt actcccgga                                       1409

<210> SEQ ID NO 6
<211> LENGTH: 960
<212> TYPE: DNA
<213> ORGANISM: Mus musculus

<400> SEQUENCE: 6
ggatttactg ctcagccagc tacttaccat cataacagca ctaccacctg gactggaagt      60
aggactgcac catacacacc taatttgcct caccaccaaa acggccatct tcagcaccac      120
ccgcctatgc cgcccccatcc tggacattac tggccagttc acaatgagct tgcattccag    180
cctcccattt ccaatcatcc tgctcctgag tactggtgct ccattgctta ctttgaaatg     240
gacgttcagg taggagagac gtttaaggtc ccttcaagtt gccctgttgt gactgtggat     300
ggctatgtgg atccttcggg aggagatcgc ttttgcttgg gtcaactctc caatgtccac     360
aggacagaag cgattgagag agcgaggttg cacataggaa aggagtgca gttggaatgt      420 aaaggtgaag gtgacgtttg ggtcaggtgc cttagtgacc acgcggtctt tgtacagagt     480
tactacctgg acagagaagc tggccgagca cctggcgacg ctgttcataa gatctaccca     540
agcgcgtata taaggtctt tgatctgcgg cagtgtcacc ggcagatgca gcaacaggcg      600
gccactgcgc aagctgcagc tgctgctcag gcggcggccg tggcagggaa catccctggc    660
cctgggtccg tgggtggaat agccccagcc atcagtctgt ctgctgctgc tggcatcggt    720
gtggatgacc tccggcgatt gtgcattctc aggatgagct ttgtgaaggg ctggggccca    780
gactacccca ggcagagcat caaggaaacc ccgtgctgga ttgagattca ccttcaccga    840
```

-continued

```
gctctgcagc tcttggatga agtcctgcac accatgccca ttgcggaccc acagccttta       900
gactgagatc tcacaccacg gacgccctaa ccatttccag gatggtggac taatgaaata       960

<210> SEQ ID NO 7
<211> LENGTH: 476
<212> TYPE: DNA
<213> ORGANISM: Mus musculus
<220> FEATURE:
<221> NAME/KEY: misc_feature
<222> LOCATION: (262)..(476)
<223> OTHER INFORMATION: n can be any nucleotide

<400> SEQUENCE: 7 ttttttttttt tccacttcgt atagtgactc agttttattt acgctagtaa ctaggtagaa       60
agtatacatg tgtgtctgtg gtacagtcaa tgtgtcttaa ctcctccact tcaatctcta       120
caaagtcacc gccaagtgat caaggatggc aaacacaggg cttataacca aaaggtataa       180
aaaagtctgc agtcttgccc taagatacaa aaactgaatt ttaaacaatg tcaaaacata       240
catgatttta acaagtatat gnaaaagaat cacacatcaa atcaagtaca aaatatccca       300
aaccacctgt tacaactgca ctgtttccat tatcctgcac agtatttaac ataaaaattt       360
agcagtttcc aaaaatattc attaattcac ttgaagttac tgccccntgc aaaacagtga       420
aacaccaggc aaaccaanct gcctttaatt nttttnnacc aaatcntcct cccnan          476

<210> SEQ ID NO 8
<211> LENGTH: 850
<212> TYPE: DNA
<213> ORGANISM: Mus musculus

<400> SEQUENCE: 8
gacagaaccg gttcgcaccg acagacggac agaggaccag acagccacta aggagcgctt       60 actgccccc tccgggcccc tgccccgaac tccagcccca gcgcctgtta ctgccccaga       120
tacagcaaga tgcgcggtcc tggcagcgag acacgggcga gcactgtccc ccggtccccg       180
agccctggcc cctagcgccc agcgctgctg ccctgcatca gggagggccg cggagacccc       240
agcctcagtt ggcgcaggag ccctgcgggt ggggcctgcc cagcccagcc aggcgcgcca       300
gcccaccatg ctcctcctgt cgccgcgcag cgcgctggtc tccgtctatt gcccgcagat       360 cttttctcctt ctgtccacgg cagttactac attgtcatcc gtggtggccc tgggagccaa       420
catcatctgc aacaagattc ctggcctggc cccacggcag cgtgccatct gccagagccg       480
acccgatgcc atcattgtga tcggggaggg ggcgcagatg ggcatcgacg agtgccagca       540
ccagttccga ttcggccgct ggaactgctc cgccctgggc gagaagaccg tcttcgggca       600
agaactccga gtagggagtc gagaggctgc cttcacctat gccatcacgg cggcgggcgt       660
ggcgcatgct gtcaccgctg cctgcagcca gggcaatctg agcaattgtg gctgtgaccg       720
ggagaagcaa ggctactaca accaggcgga aggctggaag tgggggggct gctcagcgga       780
cgtccgctac ggcatcgact tttctcgtcg ctttgtggat gcccgtgaga tcaaaaagaa       840
cgccggatcc                                                             850

<210> SEQ ID NO 9
<211> LENGTH: 475
<212> TYPE: DNA
<213> ORGANISM: Mus musculus
<220> FEATURE:
<221> NAME/KEY: misc_feature
<222> LOCATION: (446)..(446)
```

<223> OTHER INFORMATION: n can be any nucleotide

<400> SEQUENCE: 9

```
agacactgtt gtattcagat tatttcttag tggctggctt ttgattctag acagagattc    60
ttaaagtcct tttaaaaaag tggatcagga atcctgttat gggccttgat tgttccagac   120
attagaagta atatatttg atgaaggaaa tcttgaaaaa atactgacta gataaaaatt   180
gtaagccaag ctttctgact gaaaaatgct acctagccac agatcattgc tgttatttgg   240
ttcattgcat gagtgtgtat gtgtgtgtat atatgtatac acatatatat gtgtgtgtgt   300
gtgtatgtgt acacacacat atatgtgggt tttgggggggt atggataaga tggtgctatg   360
aaaataattt gtctcttgtt ttaattaatg aagcttctgt catgccaagt aatctttaag   420
ggagaatcag aacttttcat taaaantcat aagggaaaca gaatttgtac gggtg        475
```

<210> SEQ ID NO 10
<211> LENGTH: 1537
<212> TYPE: DNA
<213> ORGANISM: Mus musculus

<400> SEQUENCE: 10

```
agcggagttt cagtctgcgg acacgcgtgg agcccttgcc cgggcctccg tgggtctgag    60
gcgctgcgag ccctgggtaa ccacggcctc gagctgctgt cctcaccaag atcctccaat   120
tctgaaccaa gaacaaaaaa atgtttcagc ttcgtgcatt tcaagaagg cattaactag    180
agcccagttt ggcggacaag ttcttcattc aaaagagagt cctgttagga tcactgtgtc   240
caaaagaaac acatttgttt tgggaggcat tgattgtact tatgaaaagt ttgaaaatac   300
tgatgttaac accattagtt ctctttgtgt tcctattaag aatcatagcc aatctattac   360
ttctgataat gatgtgacaa cagaaaggac tgcaaaagag gatattacag aaccaaatga   420
agagatgatg tccagaagaa ctattcttca agatcccata aagaatacat ctaaaattaa   480
acgttcaagt ccaagaccta atttaacact atctggccgg tctcaaagaa atgtacaaa    540
gcttgaaact gttgtaaaag aagtaaaaaa atatcaggca gtccacctac aggaatggat   600
gattaaagtc atcaataata atactgctat atgtgtagaa ggaaagctgg tagatatgac   660
tgatgtttat tggcatagca atgtaattat agagcggatt aaacacaatg aacttaggac   720
cttatcaggc aacatttata tcttaaaagg attgatagac tcggtctcca tgaaagaagc   780
aggatatccc tgttatctca aagaaaatt tatgtttgga tttcccccaca actggaagga   840
acacattgat aaatttctag aacaattaag ggctgaaaaa aagaacaaga ccagacagga   900
aacagcaaga gtccaagaaa acaaaaaatc aaaaaaaaaa gatgcagaag ataaagaaac   960
ttatgtcctc caaaaggcca gcatcacgta tgaccttaat gataatagct agagagaac   1020
tgaagtaccc actgatccct tgaactcact ggaacagcct acctccggca agaaagaag   1080
acaccgctt ctcagtcaga agagagctta tgttttaata acaccactta gaaacaaaaa   1140
gttgatagag caaagatgta tagactacag tctctctatt gaaggaatat cggactttt   1200
caaagcaaag catcaagaag aaagtgactc agatatacat ggaactccaa gttctaccag   1260
taagtctcaa gagacctttg aacatagagt gggatttgaa ggcaatacca aggaggactg   1320
caatgaatgt gacataatca ctgccagaca tattcagata ccttgcccga aaagtaaaca   1380
aatgctcacc aatgatttta tgaaaagaa caagttgccc tcaaaactgc agaaaactga   1440
aaatcaaata ggtgtatcac agtattgccg gtcctcatca catttgtcaa gtgaagagaa   1500
tgaagtagaa attaaaagta gaaccagagg atcccaa                            1537
```

<210> SEQ ID NO 11
<211> LENGTH: 477
<212> TYPE: DNA
<213> ORGANISM: Mus musculus
<220> FEATURE:
<221> NAME/KEY: misc_feature
<222> LOCATION: (261)..(448)
<223> OTHER INFORMATION: n can be any nucleotide

<400> SEQUENCE: 11

```
gagtaaactc tccttccgag cgcgggcgct ggacgccgcc aaaccgctgc ccatctaccg      60
cggcaaggac atgcctgatc tcaacgactg cgtctccatc aaccgggccg tgccccagat    120
gcccaccggg atggagaagg aggaggaatc ggaacatcac ctacagcgag ctatttcagc    180
gcagcaagta tttagagaaa aaaagagag catggtcatt ccagttcctg aggcagagag     240
caacgtcaac tattacaatc ngcttgtaca aggggagtt caaacagccc aagcagttca    300
tncatattca gccttttaac ctagacaacg agcaaccaga ttatgatatg gattcagaag   360
atgagacatt attaaataga cttaacagaa aaatggaaat taaacctttg caatttgaaa   420
ttatgattga cagacttgaa aaagccantt ctaccagctt gtacacttca agaagca      477
```

<210> SEQ ID NO 12
<211> LENGTH: 572
<212> TYPE: DNA
<213> ORGANISM: Mus musculus
<220> FEATURE:
<221> NAME/KEY: misc_feature
<222> LOCATION: (505)..(572)
<223> OTHER INFORMATION: n can be any nucleotide

<400> SEQUENCE: 12

```
tctggttcta cttttaattt ctacttcatt ctcttcactt gacaaatgtg atgaggaccg      60
gcaatactgt gatacaccta tttgattttc agttttctgc agttttgagg gcaacttgtt    120
cttttttcata aaatcattgg tgagcatttg tttacttttc gggcaaggta tctgaatatg   180
tctggcagtg attatgtcac attcattgca gtcctccttg gtattgcctt caaatcccac    240
tctatgttca aggtctctt gagacttact ggtagaactt ggagttccat gtatatctga    300
gtcactttct tcttgatgct ttgctttgaa aaatccgata ttccttcaat agagagactg   360
tagtctatac atctttgctc tatcaacttt ttgtttctaa gtggtgttat taaaacataa   420
gctctcttct gactgagaag cgggtgtctt ctttcttgc cggaggtagc tgttccagtg     480
attcaaggga tcaatgggta ctcantctct ctaanctata tcataaggtc tacttaatgc   540
tggcttttgg aagantaatt ctttatctct gn                                 572
```

<210> SEQ ID NO 13
<211> LENGTH: 579
<212> TYPE: DNA
<213> ORGANISM: Mus musculus
<220> FEATURE:
<221> NAME/KEY: misc_feature
<222> LOCATION: (315)..(579)
<223> OTHER INFORMATION: n can be any nucleotide

<400> SEQUENCE: 13

```
ctgctgtgag gaatgctggg attgttgttt ctgatgaagc tgcgcaagtt gctgcctttg      60
catttgaact agctgctgtt gatgtgtctg aaactgctct tctgtgatgc ccctgttac     120
tgatatgccg ttcttgctgg tgttcaataa agctacggat gctgcagaaa ctctttact     180
```

```
gctcacagtc tgccctggtt ttcttgaggt acattcttca ctatcaatgt cctgtacatt    240
tagtagcctt ggctggaaac actgtagtcg acatgatctg atattgctta atatttcaga    300
aagagacagt ctatnttcac aaggtttact gggaagcatt ggtccgagag aaattagaag    360
aaaatctata gtttgggaag acttgaaaac ccgttcagca tctcanggtc tatctgtttc    420 aggacgggt catgttctgt ggatatccgt ccattatgaa cctgccactc tgccattccc     480
ctccttgcaa tcctatacat cttcttggac tgtaatttcg taaganatgc ttatactcaa    540
cttatccaat ctgccactct gaatttcnac atatggtan                          579

<210> SEQ ID NO 14
<211> LENGTH: 403
<212> TYPE: DNA
<213> ORGANISM: Mus musculus
<220> FEATURE:
<221> NAME/KEY: misc_feature
<222> LOCATION: (400)..(400)
<223> OTHER INFORMATION: n can be any nucleotide

<400> SEQUENCE: 14
ggaaagacaa agatgcagga tatagtactt ggaacaggct ttttaagtat tcatcctaaa     60
aatgaggctg agcacataga aaatggggct aagtgtccga atttggagtc cataaataag    120
gtaaatggtc tttgtgagga cactgcaccg tctcctggta gggttgaacc acagaaggcc    180
agttcttctg ctgacgtggg catttctaaa agcacggaag atctatctcc tcagagaagt    240
ggtccaactg gagctgttgt gaaatctcat agtataacta acatggagac tggaggctta    300
aaaatctatg acattcttgg tgatgatggc cctcagccgc caagttgcag cagttaaaat    360
cgcatctgct gtggatgggg aagaacatat cagaagcaan tct                     403

<210> SEQ ID NO 15
<211> LENGTH: 555
<212> TYPE: DNA
<213> ORGANISM: Mus musculus
<220> FEATURE:
<221> NAME/KEY: misc_feature
<222> LOCATION: (382)..(555)
<223> OTHER INFORMATION: n can be any nucleotide

<400> SEQUENCE: 15
tttttttttt tttttttttt gacagttttg aaattatatt tattaatgct ttattatacg     60
tattgtattc tatttgagcc aagggaaagg agaaccccac tcaagtgaga taacaaactt    120
gctgtctttt acaaaattta atcagaactg acaatgttat ggttagttct taattcctga    180
gaatttgaac atcattaagt tttctgtgaa tttacaacaa aacactcatg ttaatattta    240
aattacaata tttctgaaaa atattgtta gcaaagaaa accacatcca acgtatacag      300
taacccaggt gtgaacatac tgaagccctg ttgctcagca gtttaatacc atttaaatat    360
ttctctcatc agagatttat tncaaataca tgaacttatt ataatttacc agaatacagt    420
gacatnattt ttnttttttt ttaaanaatt attatctatt atatgtaagt acccggtanc    480
tgtcttcaac acccagaana agggtccaa tcttttacag aaggtgtgac cncatgtggn    540
gncgggaatt nannn                                                    555

<210> SEQ ID NO 16
<211> LENGTH: 562
<212> TYPE: DNA
<213> ORGANISM: Mus musculus
<220> FEATURE:
<221> NAME/KEY: misc_feature
```

```
<222> LOCATION: (430)..(561)
<223> OTHER INFORMATION: n can be any nucleotide

<400> SEQUENCE: 16
ctacgaaatt gtacctgagt gacataaacc ggtaaaggtg tgttacttcg cttttttcatg      60 tttttttttt cttttttgttc tttggtctga taagaaaatg gacagttgtg gaaagtcagg     120
taatacagat cagtttccag ttcagaaccc taaatcacac ctacgtgagt gaggctgctg     180
cactgctttc cttgggttct tcggccggcc agacagcctt tctgctttgt aagtgacttc     240
attatagcca tcagctaatc actccctcag catacactgg catctccaga ttacctgacg     300
gcagacatac ttgctctggc ttcaattaac atgctgtcaa gcatccctct cgacattcac     360
atggcaacac aaaaccatga atttctcttc atacaaccag gaatacacac tcataaaggg     420
aaagcgttan acctgatttt tattaaatat tatttccttc cctttccatg ccaagttcac     480
gttaacatct ttagaatact aaaacggaaa cccnccactt angaaacaac tgggaattgg     540
acatccacag gtacatcaca na                                              562

<210> SEQ ID NO 17
<211> LENGTH: 347
<212> TYPE: DNA
<213> ORGANISM: Mus musculus
<220> FEATURE:
<221> NAME/KEY: misc_feature
<222> LOCATION: (6)..(339)
<223> OTHER INFORMATION: n can be any nucleotide

<400> SEQUENCE: 17
agcggnagtt tcagtctgcg ngacacgcgt ggnagccctt gcccgggcct ccgtgggtct      60
gaggcgctgc gagccctggg taaccacggc ctcgagctgc tgtcctcacc aagatcctcc     120
aattctgaac caagaacaaa aaaatgtttc agcttcgtgc atttcaaaga aggcattaac     180
tagagcccag tttggcggac aagttcttca ttcaaaagag agtcctgtta ggatcactgt     240
gtccaaaaag aacacatttg ttttgggagg cattgattgt acttattgaa aagttttgaa     300
aatactgatg tttaacacca ttaagttctc tttgtgttnc ctaatta                   347

<210> SEQ ID NO 18
<211> LENGTH: 569
<212> TYPE: DNA
<213> ORGANISM: Mus musculus
<220> FEATURE:
<221> NAME/KEY: misc_feature
<222> LOCATION: (156)..(565)
<223> OTHER INFORMATION: n can be any nucleotide

<400> SEQUENCE: 18
cctcaatgtg tcgtagtact tgttcccgcc agtcatgagg aaccttgctt tttcctggag      60
gatctaacag agaatgttca gacccgaccc ttgtatttgg tcttttttgaa ggactagtcc    120 gtgagtaatt gaaatcacta actgacatag ttctcncngn tatttcatta atagagggac    180
gggcactctg aggcctggat gtatttgggc catcgatgct gtacgctcgt gcagaaagag    240
gtctctgtga tcctgacatg actggagttc ttcccattga atgtaactct ctgtacgata    300
agtaatctcc ttcagtacgc cttgtggggt caccgagatt tacagaagcc gttgaagaca    360
cgctactctg tctctgaata gtaatccgaa tgactgctgg cactagtcgg tcattcnggg    420 agataccccac atttctccat gcctggctgg ggcaatctct gttgtaantg gtatccaata   480
ttggtctaca ttgttatggt taaaaaaatc tgtttggaga atgctttgca tactgtnaat    540
```

```
ttctgcctcn caaatnttgg aaggnccga                                       569
```

<210> SEQ ID NO 19
<211> LENGTH: 338
<212> TYPE: DNA
<213> ORGANISM: Mus musculus
<220> FEATURE:
<221> NAME/KEY: misc_feature
<222> LOCATION: (42)..(321)
<223> OTHER INFORMATION: n can be any nucleotide

<400> SEQUENCE: 19

```
gagacattct gaagggcagg aatgaggcgc tctccccagg gnagatggtg gtgaggctgc       60
tgagggggaa ggtgatatct ttccatcttc tcattacctg ccaatcacca agaaggccc      120
tcgagacatt ctggatggca gaagtggcat ttctgtggct aacttcgacc cgggcacctt    180
tagcctgatg cgatgtgact tctgtggggc tggttttgat actcggctg gcctctccag      240
tcatgcccgg gcccaccttc gtgactttgg catcaccaac ttggggaact ccaccatctc    300
accatcaaca tccttgcaaa naacttgctg ggccacct                            338
```

<210> SEQ ID NO 20
<211> LENGTH: 483
<212> TYPE: DNA
<213> ORGANISM: Mus musculus
<220> FEATURE:
<221> NAME/KEY: misc_feature
<222> LOCATION: (318)..(481)
<223> OTHER INFORMATION: n can be any nucleotide

<400> SEQUENCE: 20

```
ggagggtgta gcaaggcctg agaacatctt ccgggccgtg ggaggaggag aagcagttgg       60
tgagtggccc agaggactgc ctggtggtgg tggcaacttc ttggtcaaag gtgagatgtg      120
aagatcagag ggacttcggg cttctagtga gctgccagga cctccagtgc tcagcacctt     180
ggccagggct tttgggctag gacctggtgg gtggaggtgt cccctggcc tggattgggt       240
ccgtctcttc aggatctccc gaagtgtgtc gatgggtgag ccgttcacat accactcagt      300
tacacccatc tggcgcangt gggaacgtgc atggctanac aagccctttc tgttctcaaa     360
gaatcaccac anaactcaca gcggatatct cttgttggct ctgggcctga ancatctccg    420
tanattggcc canggtcctc accccantta ngcgggaaag gcatggtnaa aagtaacctt    480
ngc                                                                   483
```

<210> SEQ ID NO 21
<211> LENGTH: 51
<212> TYPE: PRT
<213> ORGANISM: SBD mutant

<400> SEQUENCE: 21

Gln His Leu Gly Val Gly Met Glu Ala Pro Leu Leu Gly Phe Pro Thr
1               5                   10                  15
Met Asn Ser Asn Leu Ser Glu Val Gln Lys Val Leu Gln Ile Val Asp
            20                  25                  30
Asn Thr Val Ser Arg Gln Lys Met Asp Cys Lys Thr Glu Asp Ile Ser
        35                  40                  45
Lys Leu Lys
    50

<210> SEQ ID NO 22
<211> LENGTH: 23

```
<212> TYPE: DNA
<213> ORGANISM: F3th12F (forward primer)

<400> SEQUENCE: 22
cggcggcaga tacgcctcct gca                                        23

<210> SEQ ID NO 23
<211> LENGTH: 29
<212> TYPE: DNA
<213> ORGANISM: th12 mouse1 (reverse primer)

<400> SEQUENCE: 23
caggagcagt tgtgggtaga gccttcatc                                  29

<210> SEQ ID NO 24
<211> LENGTH: 31
<212> TYPE: DNA
<213> ORGANISM: th12

<400> SEQUENCE: 24
ctggactgag ctggacctgt ctctccagta c                               31

<210> SEQ ID NO 25
<211> LENGTH: 30
<212> TYPE: DNA
<213> ORGANISM: th12

<400> SEQUENCE: 25
cacaagggag tatttcttgc gccacgaagg                                 30

<210> SEQ ID NO 26
<211> LENGTH: 20
<212> TYPE: DNA
<213> ORGANISM: th12

<400> SEQUENCE: 26
gccatggtgt gaggagaagc                                            20

<210> SEQ ID NO 27
<211> LENGTH: 19
<212> TYPE: DNA
<213> ORGANISM: Brachyury Binding Site

<400> SEQUENCE: 27
tgacacctag gtgtgaatt                                             19
```